United States Patent
Xiang

(10) Patent No.: US 7,332,651 B2
(45) Date of Patent: Feb. 19, 2008

(54) NUCLEOTIDE SEQUENCES AND METHOD OF USING SAME TO INCREASE PLANT STRESS TOLERANCE

(76) Inventor: Chengbin Xiang, 1835 Pleasant St., West Des Moines, IA (US) 50265

( * ) Notice: Subject to any disclaimer, the term of this patent is extended or adjusted under 35 U.S.C. 154(b) by 0 days.

(21) Appl. No.: 11/483,944

(22) Filed: Jul. 10, 2006

(65) Prior Publication Data

US 2006/0253938 A1    Nov. 9, 2006

Related U.S. Application Data

(63) Continuation-in-part of application No. PCT/CN2004/000524, filed on May 24, 2004.

(30) Foreign Application Priority Data

Jan. 15, 2004    (CN) .................. 2004 1 0000682

(51) Int. Cl.
*C12N 15/82*    (2006.01)
*C12N 15/90*    (2006.01)
(52) U.S. Cl. .................. 800/289; 435/468; 800/278
(58) Field of Classification Search .............. None
See application file for complete search history.

(56) References Cited

U.S. PATENT DOCUMENTS

2006/0253938 A1* 11/2006 Xiang .................. 800/289

FOREIGN PATENT DOCUMENTS

WO    WO 03/013227 A2 * 2/2003

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Maniatis et al. (Molecular Cloning: A Laboratory Manual, Cold Spring Harbor Laboratory (1982).*
Mittler et al. (Trends in Plant Science, 11:15-19, 2006).*
Hetherington et al. (Nature, 424:901-908, 2003).*
Yamada et al. (NCBI/EMBL Database, Sequence Accession No. BT004915, Published Mar. 4, 2003).*
Valvekens et al. (PNAS, 85:5536-5540, 1988).*
Liu et al. (Eur. J. Biochem., 262:247-257, 1999).*
Sequence homology results of Ratcliffe et al. SEQ ID NOs: 1019 and 1020 with instant SEQ ID NOs: 1 and 2, respectively; pp. 1-5.*
Genbank accession No. NM_101655 "*Arabidopsis thaliana* transcription factor (AT1G17920) mRNA, complete cds." Jun. 9, 2006.
Genbank accession No. NC_003070, "*Arabidopsis thaliana* 1 cds" Jun. 9, 2006.
.Genbank accession No. CW840590 "ET10279 Ds. Oct. 6, 2002. jw42. 251 *Arabidopsis thaliana* Landsberg Ds insertion lines *Arabidopsis thailiana* genomic clone ET10279, genomic survey sequence." Nov. 26, 2004.
Genbank accession No. BZ764885 "SALK_127261 .52. 85. × *Arabidopsis thaliana* TDNA lines *Arabidopsis thaliana* genomic clones SALK_127261. 52. 85. ×, genomic survey sequence." Mar. 13, 2003.
Genbank accession No. BT004915 "*Arabidopsis thaliana* clone U20587 putative homeobox protein (At1g73360_mRNA, complete cds." Yamada, K. et al., Mar. 4, 2003.
Genbank accession No. BT004915.1; Yamada,K, et al. Feb. 14, 2003.

\* cited by examiner

*Primary Examiner*—Phuong T. Bui
*Assistant Examiner*—Vinod Kumar
(74) *Attorney, Agent, or Firm*—Patricia A. Sweeney

(57) ABSTRACT

A nucleotide sequence and encoded amino acid is shown which is a transcription factor that can be introduced into plants. The expression of the sequence of this invention in plants results in improved stress tolerance compared to plants not expressing the sequence.

8 Claims, 16 Drawing Sheets

SEQUENCE LISTING

<160> NUMBER OF SEQ ID NOS: 4

<210> SEQ ID NO 1
<211> LENGTH: 2169
<212> TYPE: DNA
<213> ORGANISM: Arabidopsis thaliana

<400> SEQUENCE: 1

| | | | | | |
|---|---|---|---|---|---|
| atgagtttcg | tcgtcggcgt | cggcggaagt | ggtagtggaa | gcggcggaga | cggtggtggt | 60 |
| agtcatcatc | acgacggctc | tgaaactgat | aggaagaaga | aacgttacca | tcgtcacacc | 120 |
| gctcaacaga | ttcaacgcct | tgaatcgagt | ttcaaggagt | gtcctcatcc | agatgagaaa | 180 |
| cagaggaacc | agcttagcag | agaattgggt | ttggctccaa | gacaaatcaa | gttctggttt | 240 |
| cagaacagaa | gaactcagct | taaggctcaa | catgagagag | cagataatag | tgcactaaag | 300 |
| gcagagaatg | ataaaattcg | ttgcgaaaac | attgctatta | gagaagctct | caagcatgct | 360 |
| atatgtccta | actgtggagg | tcctcctgtt | agtgaagatc | cttactttga | tgaacaaaag | 420 |
| cttcggattg | aaaatgcaca | ccttagaaga | gagcttgaaa | gaatgtctac | cattgcatca | 480 |
| aagtacatgg | gaagaccgat | atcgcaactc | tctacgctac | atccaatgca | catctcaccg | 540 |
| ttggatttgt | caatgactag | tttaactggt | tgtggaccct | ttggtcatgg | tccttcactc | 600 |
| gattttgatc | ttcttccagg | aagttctatg | gctgttggtc | ctaataataa | tctgcaatct | 660 |
| cagcctaact | tggctatatc | agacatggat | aagcctatta | tgaccggcat | tgcttttgact | 720 |
| gcaatggaag | aattgctcag | gcttcttcag | acaaatgaac | ctctatggac | aagaacagat | 780 |
| ggctgcagag | acattctcaa | tcttggtagc | tatgagaatg | ttttcccaag | atcaagtaac | 840 |
| cgagggaaga | accagaactt | tcgagtcgaa | gcatcaaggt | cttctggtat | tgtcttcatg | 900 |
| aatgctatgg | cacttgtcga | catgttcatg | gattgtgtca | gtggacaga | actctttccc | 960 |
| tctatcattg | cagcttctaa | aacacttgca | gtgatttctt | caggaatggg | aggtacccat | 1020 |
| gagggtgcat | tgcatttgtt | gtatgaagaa | atggaagtgc | tttcgccttt | agtagcaaca | 1080 |
| cgcgaattct | gcgagctacg | ctattgtcaa | cagactgaac | aaggaagctg | gatagttgta | 1140 |
| aacgtctcat | atgatcttcc | tcagtttgtt | tctcactctc | agtcctatag | atttccatct | 1200 |
| ggatgcttga | ttcaggatat | gcccaatgga | tattccaagg | ttacttgggt | tgaacatatt | 1260 |
| gaaactgaag | aaaagaact | ggttcatgag | ctatacagag | agattattca | cagagggatt | 1320 |
| gcttttgggg | ctgatcgttg | ggttaccact | ctccagagaa | tgtgtgaaag | atttgcttct | 1380 |
| ctatcggtac | cagcgtcttc | atctcgtgat | ctcggtggag | tgattctatc | accggaaggg | 1440 |
| aagagaagca | tgatgagact | tgctcagagg | atgatcagca | actactgttt | aagtgtcagc | 1500 |
| agatccaaca | cacacgctc | aaccgttgtt | tcggaactga | cgaagttgg | aatccgtgtg | 1560 |
| actgcacata | gagccctga | accaaacggc | acagtcctat | gtgcagccac | cactttctgg | 1620 |
| cttcccaatt | ctcctcaaaa | tgtcttcaat | ttcctcaaag | acgaaagaac | ccgtcctcag | 1680 |
| tgggatgttc | tttcaaacgg | aaacgcagtg | caagaagttg | ctcacatctc | aaacggatca | 1740 |
| catcctggaa | actgcatatc | ggttctacgt | ggatccaatg | caacacatag | caacaacatg | 1800 |
| cttattctgc | aagaaagctc | aacagactca | tcaggagcat | ttgtggtcta | cagtccagtg | 1860 |
| gatttagcag | cattgaacat | cgcaatgagc | ggtgaagatc | cttcttatat | tcctctcttg | 1920 |
| tcctcaggtt | tcacaatctc | accagatgga | aatggctcaa | actctgaaca | aggaggagcc | 1980 |
| tcgacgagct | caggacgggc | atcagctagc | ggttcgttga | taacggttgg | gtttcagata | 2040 |

```
atggtaagca atttaccgac ggcaaaactg aatatggagt cggtggaaac ggttaataac    2100
ctgataggaa caactgtaca tcaaattaaa accgccttga gcggtcctac agcttcaact    2160
acagcttga                                                            2169
```

<210> SEQ ID NO 2
<211> LENGTH: 722
<212> TYPE: PRT
<213> ORGANISM: Arabidopsis thaliana

<400> SEQUENCE: 2

```
Met Ser Phe Val Val Gly Val Gly Gly Ser Gly Ser Gly Gly
 1               5                  10                  15

Asp Gly Gly Ser His His Asp Gly Ser Glu Thr Asp Arg Lys
            20                  25                  30

Lys Lys Arg Tyr His Arg His Thr Ala Gln Gln Ile Gln Arg Leu Glu
        35                  40                  45

Ser Ser Phe Lys Glu Cys Pro His Pro Asp Glu Lys Gln Arg Asn Gln
    50                  55                  60

Leu Ser Arg Glu Leu Gly Leu Ala Pro Arg Gln Ile Lys Phe Trp Phe
65                  70                  75                  80

Gln Asn Arg Arg Thr Gln Leu Lys Ala Gln His Glu Arg Ala Asp Asn
                85                  90                  95

Ser Ala Leu Lys Ala Glu Asn Asp Lys Ile Arg Cys Glu Asn Ile Ala
            100                 105                 110

Ile Arg Glu Ala Leu Lys His Ala Ile Cys Pro Asn Cys Gly Gly Pro
        115                 120                 125

Pro Val Ser Glu Asp Pro Tyr Phe Asp Glu Gln Lys Leu Arg Ile Glu
    130                 135                 140

Asn Ala His Leu Arg Glu Glu Leu Glu Arg Met Ser Thr Ile Ala Ser
145                 150                 155                 160

Lys Tyr Met Gly Arg Pro Ile Ser Gln Leu Ser Thr Leu His Pro Met
                165                 170                 175

His Ile Ser Pro Leu Asp Leu Ser Met Thr Ser Leu Thr Gly Cys Gly
            180                 185                 190

Pro Phe Gly His Gly Pro Ser Leu Asp Phe Asp Leu Leu Pro Gly Ser
        195                 200                 205

Ser Met Ala Val Gly Pro Asn Asn Leu Gln Ser Gln Pro Asn Leu
    210                 215                 220

Ala Ile Ser Asp Met Asp Lys Pro Ile Met Thr Gly Ile Ala Leu Thr
225                 230                 235                 240

Ala Met Glu Glu Leu Leu Arg Leu Leu Gln Thr Asn Glu Pro Leu Trp
                245                 250                 255

Thr Arg Thr Asp Gly Cys Arg Asp Ile Leu Asn Leu Gly Ser Tyr Glu
            260                 265                 270

Asn Val Phe Pro Arg Ser Ser Asn Arg Gly Lys Asn Gln Asn Phe Arg
        275                 280                 285

Val Glu Ala Ser Arg Ser Ser Gly Ile Val Phe Met Asn Ala Met Ala
    290                 295                 300

Leu Val Asp Met Phe Met Asp Cys Val Lys Trp Thr Glu Leu Phe Pro
305                 310                 315                 320

Ser Ile Ile Ala Ala Ser Lys Thr Leu Ala Val Ile Ser Ser Gly Met
                325                 330                 335

Gly Gly Thr His Glu Gly Ala Leu His Leu Leu Tyr Glu Glu Met Glu
```

```
                340             345             350
Val Leu Ser Pro Leu Val Ala Thr Arg Glu Phe Cys Glu Leu Arg Tyr
            355                 360                 365

Cys Gln Gln Thr Glu Gln Gly Ser Trp Ile Val Val Asn Val Ser Tyr
        370                 375                 380

Asp Leu Pro Gln Phe Val Ser His Ser Gln Ser Tyr Arg Phe Pro Ser
385                 390                 395                 400

Gly Cys Leu Ile Gln Asp Met Pro Asn Gly Tyr Ser Lys Val Thr Trp
                405                 410                 415

Val Glu His Ile Glu Thr Glu Lys Glu Leu Val His Glu Leu Tyr
            420                 425                 430

Arg Glu Ile Ile His Arg Gly Ile Ala Phe Gly Ala Asp Arg Trp Val
                435                 440                 445

Thr Thr Leu Gln Arg Met Cys Glu Arg Phe Ala Ser Leu Ser Val Pro
            450                 455                 460

Ala Ser Ser Ser Arg Asp Leu Gly Gly Val Ile Leu Ser Pro Glu Gly
465                 470                 475                 480

Lys Arg Ser Met Met Arg Leu Ala Gln Arg Met Ile Ser Asn Tyr Cys
                485                 490                 495

Leu Ser Val Ser Arg Ser Asn Asn Thr Arg Ser Thr Val Val Ser Glu
            500                 505                 510

Leu Asn Glu Val Gly Ile Arg Val Thr Ala His Lys Ser Pro Glu Pro
        515                 520                 525

Asn Gly Thr Val Leu Cys Ala Ala Thr Thr Phe Trp Leu Pro Asn Ser
    530                 535                 540

Pro Gln Asn Val Phe Asn Phe Leu Lys Asp Glu Arg Thr Arg Pro Gln
545                 550                 555                 560

Trp Asp Val Leu Ser Asn Gly Asn Ala Val Gln Glu Val Ala His Ile
                565                 570                 575

Ser Asn Gly Ser His Pro Gly Asn Cys Ile Ser Val Leu Arg Gly Ser
            580                 585                 590

Asn Ala Thr His Ser Asn Asn Met Leu Ile Leu Gln Glu Ser Ser Thr
        595                 600                 605

Asp Ser Ser Gly Ala Phe Val Val Tyr Ser Pro Val Asp Leu Ala Ala
    610                 615                 620

Leu Asn Ile Ala Met Ser Gly Glu Asp Pro Ser Tyr Ile Pro Leu Leu
625                 630                 635                 640

Ser Ser Gly Phe Thr Ile Ser Pro Asp Gly Asn Gly Ser Asn Ser Glu
                645                 650                 655

Gln Gly Gly Ala Ser Thr Ser Ser Gly Arg Ala Ser Ala Ser Gly Ser
            660                 665                 670

Leu Ile Thr Val Gly Phe Gln Ile Met Val Ser Asn Leu Pro Thr Ala
        675                 680                 685

Lys Leu Asn Met Glu Ser Val Glu Thr Val Asn Asn Leu Ile Gly Thr
    690                 695                 700

Thr Val His Gln Ile Lys Thr Ala Leu Ser Gly Pro Thr Ala Ser Thr
705                 710                 715                 720

Thr Ala

<210> SEQ ID NO 3
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 3
atgagtttcg tcgtcggcgt                                                    20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcaagctgta gttgaagctg t                                                  21
```

NUCLEOTIDE SEQUENCES AND METHOD OF USING SAME TO INCREASE PLANT STRESS TOLERANCE

RELATED APPLICATION

This application is a continuation-in-part of previously filed and co-pending PCT application PCT/CN2004/000524, filed May 24, 2004, which claims priority to Chinese application CN20040000682.2, filed Jan. 15, 2004, the disclosures of which are all incorporated herein by reference.

TECHNICAL FIELD

Disclosed here is a gene encoding a plant transcription factor, and its application in the field of gene engineering, and its application for crop improvement with stress tolerance.

TECHNOLOGY BACKGROUND

During the growth and development of plants, unfavorable environmental conditions can be considered as environmental stresses, generally divided into biotic stress and abiotic stress. Biotic stress is caused by living organisms which can harm plants, such as viruses, fungi, bacteria, and harmful insects. Abiotic stress is caused by nonliving environmental factors that can have harmful effects on plants. This includes, for example, unfavorable conditions of water, temperature, salt, light, nutrition, wind, and the like.

The negative impact that the environmental stresses bring to the agricultural production is worldwide, and the impact caused by the abiotic stress, especially drought, is even worse (Boyer J S. 1982. Plant productivity and environment. Science 218:443-448). As Table 1 shows, abiotic stresses can reduce crop yields by 50% to 80%. Effort has been poured into the research of abiotic stress biology worldwide in order to discover key abiotic stress tolerance genes and unravel the molecular mechanisms underlying stress tolerance for crop improvement by gene engineering.

TABLE 1

The average yield and the record high yield of eight different crops

| Crop | The record high yield (kg/ha) | The average yield (kg/ha) | The average loss (kg/ha) Biotic stress | The average loss (kg/ha) Abiotic stress | The loss caused by abiotic stress (% of record high yield) |
|---|---|---|---|---|---|
| maize | 19,300 | 4,600 | 1,952 | 12,700 | 65.8 |
| wheat | 14,500 | 1,880 | 726 | 11,900 | 82.1 |
| soybean | 7,390 | 1,610 | 666 | 5,120 | 69.3 |
| broomcorn | 20,100 | 2,830 | 1,051 | 16,200 | 80.6 |
| oat | 10,600 | 1,720 | 924 | 7,960 | 75.1 |
| barley | 11,400 | 2,050 | 765 | 8,590 | 75.4 |
| potato | 94,100 | 28,300 | 17,775 | 50,900 | 54.1 |
| beet | 121,000 | 42,600 | 17,100 | 61,300 | 50.7 |

Agriculture occupies a large sector in the economy of China, but abiotic stresses are major threats of Chinese agriculture, especially drought and salt stress being the two most important factors limiting sustainable agriculture. In China, 50% of arable farmland is affected by drought. Even in central and southern China with more rainfall, drought still occurs during the reproductive phase of rice, the predominant crop in the region and causes tremendous yield loss. In a severe drought, the entire crop yield may be lost. Insufficient rainfall in the vast area of northern and northwestern China makes the soil salinity problem even worse, which has become one of the major restraints of sustainable agriculture in the region.

The research of abiotic stress biology and cloning of stress tolerance gene are thus very important and urgent. Plant biologists worldwide work very hard to unravel the molecular mechanisms and isolate stress tolerance genes for crop improvement. Progress has been made, especially in the field of the molecular mechanism of salt stress by using the model plant *Arabidopsis thaliana*. Recently there were many important new discoveries (Zhu J K. 2002. Salt and drought stress signal transduction in plants. Annu. Rev. Plant Biol. 53:1247-273; Xiong L M, Schumaker K S, Zhu J K. 2002. Cell signaling during cold, drought, and salt stress. Plant Cell, S165-S183). For higher plants, sophisticated mechanisms have evolved to perceive the physical and chemical changes in their surrounding environment, and respond correspondingly by transducing the extracellular signals into the intracellular signals, and eventually relay the signals into nucleus and activate transcription factors that turn on corresponding gene expression, deploying their defense arsenals and adjusting their growth and development in order to adapt to the changed environment. Due to the complex nature of drought and salt stress effects, the molecular mechanisms underlying plant tolerance to these stresses are not fully understood although significant progress has been made (Ingram and Bartels 1996; Bray 1997; Bohnert 2000; Cushman and Bohnert 2000; Hasegawa et al. 2000; Bartels and Salamini 2001; Zhu 2002; Seki et al. 2003; Bray 2004; Amtmann et al. 2005; Zhang et al. 2005). The adaptive responses to these water deficit stresses must be coordinated at the molecular, cellular, and whole-plant levels. It is generally believed that roots first perceive a dehydration stress signal when the water deficit reaches a certain level. But how the physical signals of dehydration stress are perceived by the roots and converted into biochemical signals still remains unclear. Abscisic acid (ABA) is involved in coordinating whole plant responses since it is synthesized in the roots and translocated to the aerial portion of the plant, where it regulates stomatal behavior (Sauter et al. 2001). However, ABA receptors remained elusive until recently. One ABA receptor has finally been identified (Razem et al. 2006).The research on plant drought stress has been focused on the aspects of osmoregulation and the signal transduction of abscisic acid (ABA) and the loss-of-function mutants of *Arabidopsis thaliana* played an important role to this research (Zhu J K. 2002. Salt and drought stress signal transduction in plants. Annu. Rev. Plant Biol. 53:1247-273; Xiong L M, Schumaker K S, Zhu J K. 2002. Cell signaling during cold, drought, and salt stress. Plant Cell. S165-S183). Transpirational water loss through the stomata is an important determining factor of drought tolerance (Xiong et al. 2002 Plant Cell 14 Suppl: S165-183). Regulation of stomatal behavior has been an active area of research for drought stress, and much progress has been made (Luan 2002 Plant Cell Environ 25(2): 229-237). Root growth is another determining factor for drought tolerance (Malamy 2005 Plant Cell Environ 28(1): 67-77). Drought stress stimulates the growth of roots to extend to deeper soil to absorb water (Eapen et al. 2005 Trends Plant Sci 10(1): 44-50). Many studies have correlated root growth with drought tolerance (Zheng et al. 2000 Genome 43(1): 53-61). However, little is known about specific genes that are important for root growth under drought stress. Consequently, it has not been possible to engineer drought tolerance by enhancing root growth.

Genetic screening and analysis of loss-of-function mutants have helped us understand the plant stress tolerance mechanisms (Ishitani et al. 1997 Plant Cell 9(11): 1935-1949). However, for many genes, loss-of-function mutations do not lead to identifiable phenotypes due to functional redundancy. In addition, for some genes, loss-of-function mutations may be lethal. Gain-of-function mutants may overcome these shortcomings. Activation tagging is an effective method to generate gain-of-function mutants (Walden et al. 1994 Plant Mol Biol 26(5): 1521-1528; Weigel et al. 2000 Plant Physiol 122(4): 1003-1013).

The activation tagging method has been used successfully in identifying a number of gain-of-function mutants in plant development or hormonal responses (Kakimoto 1996; Kardailsky et al. 1999 Science 286(5446): 1962-1965; Borevitz et al. 2000 Plant Cell 12(12): 2383-2394; Ito and Meyerowitz 2000 Plant Cell 12(9): 1541-1550; Lee et al. 2000 Genes Dev 14(18): 2366-2376; van der Graaff et al. 2000 Development 127(22): 4971-4980; Huang et al. 2001 Plant Physiol 125(2): 573-584; Zhao et al. 2001 Science 291 (5502): 306-309; Razem et al. 2006 Nature 439(7074): 290-294). However, despite the power of the activation tagging approach, it has not been adequately explored for drought tolerance studies. Only a few activation tagged gain-of-function mutants with enhanced abiotic stress tolerant phenotype have been reported (Furini et al. 1997 Embo J 16(12): 3599-3608; Ahad et al. 2003 Transgenic Res 12(5): 615-629; Grant et al. 2003 Mol Plant Microbe Interact 16(8): 669-680; Aharoni et al. 2004 Plant Cell 16(9): 2463-2480; Chini et al. 2004. Plant J 38(5): 810-822). In contrast to the loss-of-function mutant, the gain-of-function mutants have not been adequately explored although the mutants can provide valuable materials for stress tolerance gene discovery and the cloned gene can be directly used for crop improvement.

SUMMARY OF THE INVENTION

A gene encoding a transcription factor and the protein sequence so encoded is provided.

The transcription factor gene of provided by this invention, named ATHD/START1 (or HS1 in short) and originated from the *Arabidopsis thaliana* mutant hs1, includes the following nucleotide sequences:

1) a nucleotide sequence of SEQ ID NO: 1;
2) a nucleotide sequence encoding the amino acid of SEQ ID NO: 2 in the sequence table;
3) a nucleotide sequence with more than 80% homology to the sequence of SEQ ID NO: 1 or a sequence encoding SEQ ID NO: 2;
4) a nucleotide sequence having more than 80% identity to the sequence of SEQ ID NO: 1 or a sequence encoding SEQ ID NO: 2;
5) a sequence which hybridizes to SEQ ID NO: 1 or a sequence encoding SEQ ID NO: 2 under highly stringent conditions of a wash of 0.1 SSC, 0.1% (w/v) SDS at 65° C.;
6) a functional fragment of the foregoing sequences which fragment and which retains the function of increasing stress tolerance in a plant compared to a plant in which the sequence has not been introduced;
7) a functional variant of the foregoing sequences which variant retains the function of increasing stress tolerance in a plant compared to a plant in which the sequence has not been introduced.

The sequence of cDNA in the SEQ ID NO: 1 is composed of 2169 bases, whose open reading frame begins from $1^{st}$ base of 5' end and ends in $2169^{th}$ base.

The transcription factor AtHD/START1, encodes the protein with the sequence of amino acid residues in SEQ ID NO: 2, or is any protein derived from the protein of SEQ ID NO: 2 which has one or several amino acid residues substituted, deleted or inserted but retains the function of improving stress tolerance in plants compared to plants in which the sequence has not been introduced.

The sequence of amino acid residues for the protein as shown in SEQ ID NO: 2 is made up of 722 amino acid residues.

Plants, plant parts and tissue, plant cells, expression vectors or cell lines with this invented gene are also set forth herein.

By using any suitable vectors and feasible means of transformation for heterologous expression, the AtHD/START1 gene can be integrated in the recipient plant genome and expressed in the transgenic plants. As a result, the transgenic plants can confer improved tolerance to drought, salt, and oxidative stress. The gene regulates root architecture by providing deeper roots, more lateral roots, and increased root biomass, as compared to plants in which the sequence has not been introduced. Further, the sequence regulates stomatal density by reducing density and allowing for increased water use efficiency and drought tolerance. Stress signals mediate the HS1 stress response. In order to select and identify the transformed plant cells and transgene plants, appropriate marker genes such as antibiotic resistance genes can be added to the construct vectors. The host plants can be any plant, including monocots or dicots such as rice, wheat, maize, cucumber, tomato, aspen, grass, clover and so on.

All references cited herein are incorporated herein by reference.

DETAILED DESCRIPTION

Figure 1:
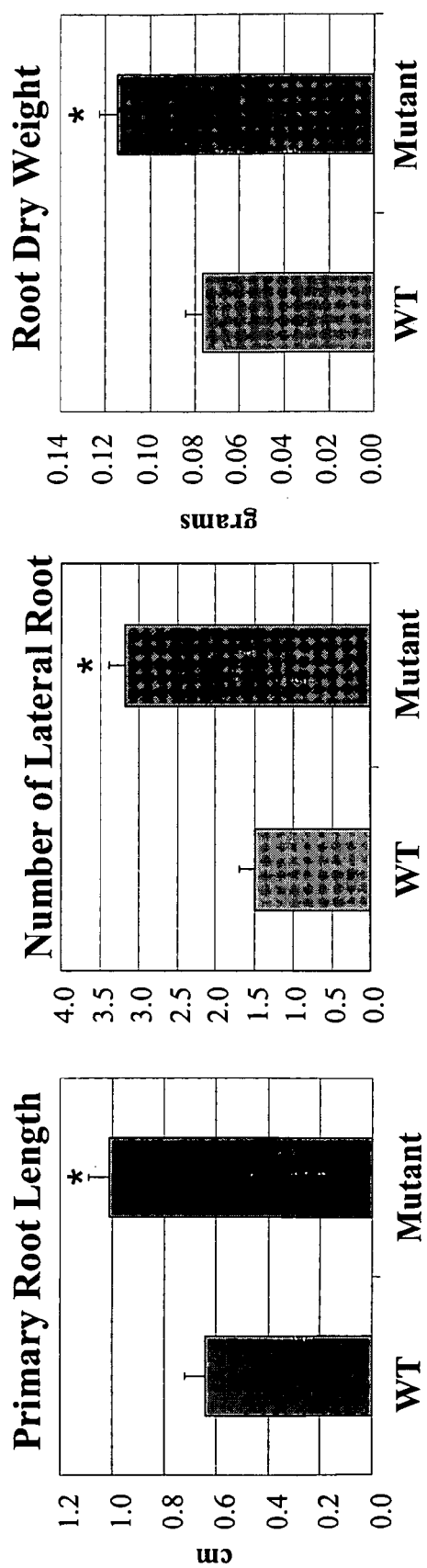
FIG. 1 is a graph showing comparison of the primary root length, the number of lateral roots and the biomass of root system between the gain-of-function mutant and the wild type. The asterisk indicates statistically significant differences *P<0.05.

We report here the identification of a novel drought tolerance gene in *Arabidopsis*, HS1, via activation tagging. HS1 encodes a protein in the HD-START transcription factor family. The activation of HS1 expression enhances multiple drought tolerance related pathways and characteristics, including enhanced root growth. The examples demonstrate the utility of a novel transcription factor gene in dramatically improving drought tolerance in a model plant, and suggests that many drought tolerance effector genes are under regulatory control of a HD-START transcription factor. Thus the gene is useful in improving abiotic stress tolerance of a plant when compared to a plant that does not express the gene.

While the invention in certain aspects discusses the usefulness of the gene in impacting stress tolerance, it is evident to one skilled in the art that the gene may be used in a variety of processes and forms. For example, fragments of the gene may be used as probes, especially to locate functional sequences in other plants, it may be mutated, introduced in an antisense version, used with hairpin formations, with promoters other than the native promoter, linked with other sequences to control its expression, or any of the many variations available to the skilled person. One skilled in the art readily appreciates that the sequence can be used with any of a variety of additional nucleotide sequences to be expressed in plants. For example, one or more other genes of interest may be expressed along with the transcription factor, and encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. DNA sequences native to plants as well as non-native DNA sequences can be transformed into plants and used to modulate levels of native or non-native proteins.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989. Molecular Cloning: A Laboratory Manual, $2^{nd}$ Edition. Cold Spring Harbor Laboratory Press, Plainview, N.Y.).

The sequences of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers.

The sequence of the invention may be obtained from other plants, according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

Thus the invention also includes those nucleotide sequences which selectively hybridize to the HS1 nucleotide sequences under stringent conditions. In referring to a sequence that "selectively hybridizes" with HS1, the term includes reference to hybridization, under stringent hybridization conditions, of a nucleic acid sequence to the specified nucleic acid target sequence to a detectably greater degree than its hybridization to non-target nucleic acid.

The terms "stringent conditions" or "stringent hybridization conditions" includes reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

In general, sequences that correspond to the nucleotide sequences of the present invention and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

Preferred hybridization conditions for the nucleotide sequence of the invention include hybridization at 42° C. in 50% (w/v) formamide, 6×SSC, 0.5% (w/v) SDS, 100 (g/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 0.1×SSC, 0.1% (w/v) SDS, at 65° C. for 30 minutes to one hour and repeating. Sequences that correspond to the sequence of the present invention may be obtained using all the above conditions. For purposes of defining the invention, the high stringency conditions are used.

The following terms are used to describe the sequence relationships between two or more nucleic acids or polynucleotides: (a) "reference sequence", (b) "comparison window", (c) "sequence identity", and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, or 100 nucleotides in length, or longer. Those of skill in the art understand that to avoid a high similarity to a reference sequence due to inclusion of gaps in the polynucleotide sequence a gap penalty is typically introduced and is subtracted from the number of matches.

Methods of aligning sequences for comparison are well-known in the art. Thus, the determination of percent sequence identity between any two sequences can be accomplished using a mathematical algorithm. Non-limiting examples of such mathematical algorithms are the algorithm of Myers and Miller (1988) CABIOS 4: 11-17; the local alignment algorithm of Smith et al. (1981) Adv. Appl. Math. 2: 482; the global alignment algorithm of Needleman and Wunsch (1970) J. Mol. Biol. 48: 443-453; the search-for-local-alignment-method of Pearson and Lipman (1988) Proc. Natl. Acad. Sci. 85: 2444-2448; the algorithm of Karlin and Altschul (1990) Proc. Natl. Acad. Sci. USA 87: 2264, modified as in Karlin and Altschul (1993) Proc. Natl. Acad. Sci. USA 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73: 237-244 (1988); Higgins et al. (1989) CABIOS 5: 151-153; Corpet et al. (1988) Nucleic Acids Res. 16: 10881-90; Huang et al. (1992) CABIOS 8: 155-65; and Pearson et al. (1994) Meth. Mol. Biol. 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215: 403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2; and the BLOSUM62 scoring matrix or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

"Functional variants" of the sequence are also encompassed by the compositions of the present invention. Functional variants include, for example, the sequences of the invention having one or more nucleotide substitutions, deletions or insertions. Functional variants of the invention may be created by site-directed mutagenesis, induced mutation, or may occur as allelic variants (polymorphisms). These functional variants retain the property of improving stress tolerance in plants compared to plants not expressing the sequence.

"Functional fragments" of the sequence are also encompassed by the compositions of the present invention. As used herein, a "functional fragment" of the sequence is a nucleotide sequence that is a formed by one or more deletions from a larger sequence. Such fragments are those that retain the function of increasing stress tolerance in plants compared to plants not expressing the sequence. Activity can be measured by Northern blot analysis, reporter activity measurements when using transcriptional fusions, and the like. See, for example, Sambrook et al. (1989) Molecular Cloning: A Laboratory Manual (2nd ed. Cold Spring Harbor Laboratory, Cold Spring Harbor, N.Y.). As used herein, reference to a functional fragment includes truncations of the gene, which retain the function of increasing stress tolerance in plants compared to plants not having the sequence.

Functional fragments can be obtained, for example, by use of restriction enzymes to cleave the naturally occurring regulatory element nucleotide sequences disclosed, by synthesizing a nucleotide sequence from the naturally occurring DNA sequence, or can be obtained through the use of PCR technology. See for example, Mullis et al. (1987) Methods Enzymol. 155:335-350, and Erlich, ed. (1989) PCR Technology (Stockton Press, New York).

The sequences of the invention may be used in conjunction with other heterologous genes introduced into the plant for any of a variety of reasons, such as agronomic improvements, selectable markers, causing changes in plant fertility, or the like.

The invention includes vectors with the HS1 gene. A vector is typically prepared comprising HS1, a promoter that will drive expression of the gene in the plant and a terminator region. In this regard, any plant-compatible promoter elements can be employed in the construct, influenced by the end result desired. Those can be plant gene promoters, such as, for example, the promoter for the small subunit of ribulose-1,5-bis-phosphate carboxylase, or promoters from the tumor-inducing plasmids from *Agrobacterium tumefaciens,* such as the nopaline synthase and octopine synthase promoters, or viral promoters such as the cauliflower mosaic virus (CaMV) 19S and 35S promoters or the figwort mosaic virus 35S promoter. See Kay et al., (1987) Science 236:1299 and European patent application No. 0 342 926; the barley lipid transfer protein promoter, LTP2 (Kalla et al., Plant J. (1994) 6(6): 849-60); the ubiquitin promoter (see for example U.S. Pat. No. 5,510,474); the END2 promoter (Linnestad et al. U.S. Pat. No. 6,903,205); and the polygalacturonase PG47 promoter (See Allen and Lonsdale, Plant J. (1993) 3:261-271; WO 94/01572; U.S. Pat. No. 5,412,085) and rice actin promoter (McElroy et al. (1990) Plant Cell 2:163-171). See international application WO 91/19806 for a review of various plant promoters also suitably employed in the present invention.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the instant invention. See Ward et al. Plant Mol. Biol. 22: 361-366 (1993). Exemplary inducible promoters include ecdysone receptor promoters, U.S. Pat. No. 6,504,082; promoters from the ACE1 system which responds to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156).

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. Examples of these type of promoters include seed preferred expression such as that provided by the phaseolin promoter (Bustos et al. 1989. The Plant Cell Vol. 1, 839-853), and the maize globulin-1 gene, Belanger, et al. 1991 Genetics 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. there are a wide variety of tissue-preferred promoters and, by way of example, include those described in Yamamoto et al. (1997) Plant J. 12(2): 255-265; Kawamata et al. (1997) Plant Cell Physiol. 38(7): 792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascini et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol Biol. 23(6): 1129-1138; Matsuoka et al. (1993) Proc Natl. Acad. Sci. USA 90(20): 9586-9590; and Guevara-Garcia et al. (1993) Plant J. 4(3): 495-505.

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in Method in Plant Molecular Biology and Biotechnology, Glick et al eds;CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens,* such as the octopine synthase and nopaline synthase (nos) termination regions (Depicker et al., Mol. and Appl. Genet. 1:561-573 (1982)). See also, Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al. Nucleic Acids Res. 17:7891-7903 (1989); Joshi et al. Nucleic Acid Res. 15:9627-9639 (1987).

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. EMBO J. 2:987-992(1983); methotrexate, Herrera Estrella et al. Nature 303:209-213(1983); Meijer et al. Plant Mol. Biol. 16:807-820 (1991); hygromycin, Waldron et al. Plant Mol. Biol. 5:103-108 (1985), Zhijian et al. Plant Science 108:

219-227 (1995); streptomycin, Jones et al. Mol. Gen. Genet. 210:86-91(1987); spectinomycin, Bretagne-Sagnard et al. Transgenic Res. 5:131-137 (1996); bleomycin, Hille et al. Plant Mol. Biol. 7:171-176 (1990); sulfonamide, Guerineau et al. Plant Mol. Biol. 15:127-136(1990); bromoxynil, Stalker et al. Science 242:419-423 (1988); glyphosate, Shaw et al. Science 233:478-481(1986); and phosphinothricin, DeBlock et al. EMBO J. 6:2513-2518 (1987). The latter is the phosphinothricin acetyl transferase ("PAT") or maize optimized PAT or bar gene confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. Other screenable markers include the anthocyanin/flavonoid genes in general (See discussion at Taylor and Briggs, The Plant Cell (1990) 2:115-127) including, for example, a R-locus gene, which encodes a product that regulates the production of anthocyanin pigments (red color) in plant tissues (Dellaporta et al., in Chromosome Structure and Function, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Scheffler et al. Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al, Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others. Yet further examples of suitable markers include the cyan fluorescent protein (CYP) gene (Bolte et al. (2004) J. Cell Science 117: 943-54 and Kato et al. (2002) Plant Physiol 129: 913-42), the yellow fluorescent protein gene (PhiYFP™ from Evrogen; see Bolte et al. (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed genes where plant cells transformed with the marker gene are red in color, and thus visually selectable (Dietrich et al. (2002) Biotechniques 2(2):286-293). Additional examples include a p-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available to one skilled in the art.

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. Proc. Nat. Acad. Sci. USA 86:6126-6130 (1989); potyvirus leaders, for example, TEV leader (Tobacco Etch Virus), Allison et al.; MDMV leader (Maize Dwarf Mosaic Virus), Virology 154:9-20 (1986); human immunoglobulin heavy-chain binding protein (BiP), Macejak et al. Nature 353:90-94 (1991); untranslated leader from the coat protein mRNA of alfalfa mosaic virus (AMV RNA 4), Jobling et al. Nature 325:622-625 (1987); Tobacco mosaic virus leader (TMV), Gallie et al. (1989) Molecular Biology of RNA, pages 237-256; and maize chlorotic mottle virus leader (MCMV) Lommel et al. Virology 81:382-385 (1991). See also Della-Cioppa et al. Plant Physiology 84:965-968 (1987).

The cassette can also contain sequences that enhance translation and/or mRNA stability such as introns. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. Plant physiol 117(4):1235-1252 (1998); Sullivan et al. Plant Cell 3(12):1337-48; Sullivan et al., Planta (1995) 196(3):477-84; Sullivan et al., J. Biol. Chem. (1992) 267 (26): 18999-9004) and the like. One skilled in the art will readily appreciate the many options available in expressing a product to a particular organelle. For example, the barley alpha amylase sequence is often used to direct expression to the endoplasmic reticulum (Rogers, J. Biol. Chem. 260: 3731-3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, Bio/Technology 10:268 (1992); and Weising et al., Ann. Rev. Genet. 22: 421-477 (1988). For example, the DNA construct may be introduced into the genomic DNA of the plant cell using techniques such as microprojectile-mediated delivery, Klein et al., Nature 327: 70-73 (1987); electroporation, Fromm et al., Proc. Natl. Acad. Sci. 82: 5824 (1985); polyethylene glycol (PEG) precipitation, Paszkowski et al., EMBO J. 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, Mol. Gen. Genetics 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (*Zea mays* L.) mediated by *Agrobacterium tumefaciens*" Nature Biotechnology 14:745-750 (1996). The virulence functions of the *Agrobacterium tumefaciens* host will direct the insertion of the construct into the plant cell DNA when the cell is infected by the bacteria. See, for example Horsch et al., Science 233: 496-498 (1984), and Fraley et al., Proc. Natl. Acad. Sci. 80: 4803 (1983).

Standard methods for transformation of canola are described at Moloney et al. "High Efficiency Transformation of *Brassica napus* using *Agrobacterium* Vectors" Plant Cell Reports 8:238-242 (1989). Corn transformation is described by Fromm et al, Bio/Technology 8:833 (1990) and Gordon-Kamm et al, supra. *Agrobacterium* is primarily used in dicots, but monocots can be transformed by *Agrobacterium*. See supra and U.S. Pat. No. 5,550,318. Rice transformation is described by Hiei et al., "Efficient Transformation of Rice (*Oryza sativs* L.) Mediated by *Agrobacterium* and Sequence Analysis of the Boundaries of the T-DNA" The Plant Journal 6(2): 271-282 (1994, Christou et al, Trends in Biotechnology 10:239 (1992) and Lee et al, Proc. Nat'l Acad. Sci. USA 88:6389(1991). Wheat can be transformed by techniques similar to those used for transforming corn or rice. *Sorghum* transformation is described at Casas et al, supra and sorghum by Wan et al, Plant Physicol. 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art. For a discussion of plant breeding techniques, see Poehlman (1995) Breeding Field Crops. AVI Publication Co., Westport Conn., 4$^{th}$ Edit.

Backcrossing methods may be used to introduce a gene into the plants. This technique has been used for decades to introduce traits into a plant. An example of a description of this and other plant breeding methodologies that are well known can be found in references such as Poelman, supra, and Plant Breeding Methodology, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

One skilled in the art appreciates that there are many variations on the components and processes with which the nucleotide sequence of the invention may be used. The following is intended to be illustrative without limiting the scope of the invention.

EXAMPLE 1

The Screening, Phenotypic Characterization of the Gain-of-function Mutant

For isolating the gain-of-function mutant, the inventor generated an *Arabidopsis thaliana* T-DNA activation tagging mutant library of ~55000 independent lines with use of the T-DNA mutagen pSKI015 an activation-tagging vector having the CaMV35S enhancers and the Bar gene which confers Basta resistance for selection. (Weigel et al., 2000. Activation tagging in *Arabidopsis*. Plant Physiol. 122:1003-13.). Briefly, wild-type Columbia plants were transformed by the floral dip method. About 120 grams of T1 seeds were bulk produced, and a transformation frequency of about 1% was achieved. The bulk seeds were selected for herbicide resistance in soil with 0.2% commercial glufosinate ammonium herbicide and screened for individuals with increased growth vigor. A few such putative mutants were isolated, and their offspring were later tested for their tolerance to drought stress. T$_2$ seeds were collected as individual pools of approximately 2000 independent lines.

The putative growth vigor mutants were subjected to drought stress under greenhouse conditions. T$_2$ plants were first selected for herbicide resistance with herbicide spray. The resistance plants were transferred to soil pots and grown side by side with the same age wildtype plants in the greenhouse. When plants were about 2 weeks old, watering was withheld until severe shoot wilting occurred. Compared with wild-type plants, mutants with improved drought tolerance were visually scored. One of the mutants showed improved drought tolerance. This mutant was later designated as hs1, for the T-DNA tagged gene At1g73360 coding for a homeodomain START protein.

Under long daylight conditions, when five weeks old this mutant shows vigorous vegetative growth and has four times more rosette leaf numbers than the wild type. Its rosette is more tightly arranged and leaf petiole is shorter than that of the wild type. Under short daylight conditions, the mutant shows similar morphology to the wild type but still has more leaf numbers. Under both conditions, the mutant flowers later than the wildtype.

There is a distinct difference in root architecture between the mutant and the wild type. The primary root of the mutant grows faster than that of the wild type and significantly longer than that of the wild type. The primary root length of one-week old mutant seedlings is almost twice as that of the wild type. In addition, the mutant has significantly more lateral roots, twice as many as the wildtype. Root biomass of the mutant is also significantly higher than that of the wildtype. The enhanced root system was also observed for mutants grown in soil under short-day conditions as seen by a markedly increased primary root length and root biomass. The tap root of the mutant was approximately twice (0.6 vs. 1.0 cm) that of wild-type plants and the root biomass of the mutant was more than 2-fold that of the wild type.

One interesting characteristic of this mutant is that the homozygote shows a markedly different phenotype between a homozygote and a heterozygote in comparison to the wild type, when grown under long-day conditions. The homozygote has more rosette leaves than the heterozygote, but the size of the leaf is much smaller. Hence, the size of the plant is markedly reduced. In addition, the homozygote flowered even later than the heterozygote and usually had only a primary bolt, with fewer siliques and setting fewer seeds. In the greenhouse, the homozygote accumulated more pigments in leaves and as a result, usually appeared purple. All subsequent experiments were carried out using the heterozygous hs1 mutant, unless specified otherwise.

Taken together, the above described mutant phenotype, especially the root architecture are just what is being sought for the agronomic improvements of many crops, horticultural plants, turf grasses, and grassland species.

EXAMPLE 2

Drought Tolerance Assay for the Gain-of-function Mutant

1. Comparison of the Response to Drought Stress Between the Wild Type and the Mutant Seedlings Mutant hs1 seedlings showed improved drought tolerance compared with wild-type seedlings and better recovery upon re-watering after severe drought stress. Under the same growth conditions, wild-type seedlings showed wilting symptom about 4 days earlier than the mutant seedlings. After drought stress (without watering) for two weeks, nearly 100% of the mutant seedlings were still alive, while none of the wild-type seedlings were.

To genetically characterize the mutant, the wild-type Columbia as the female parent was crossed with the heterozygous mutant as the male parent. $F_1$ progeny were examined for herbicide resistance and drought tolerance. A 1:1 segregation ratio (Table 2) indicates that the drought-tolerance trait was stably inherited in a Mendelian fashion and determined by a single dominant locus that co-segregated with the BAR-encoded herbicide resistance on the T-DNA.

TABLE 2

Genetic analysis of drought tolerance in hs1 mutant.

| | Tolerant | Sensitive | $\chi^2$ (1:1) |
|---|---|---|---|
| Herbicide resistance | 55 | 60 | 0.217 |
| Drought tolerance | 55 | 60 | |

The co-segregation between drought tolerance and herbicide resistance was further analyzed. A heterozygous mutant was selfed, and its progeny underwent drought-tolerance and herbicide-resistance assays. Drought tolerance assays were carried out for both seedlings and 4-week-old plants. For seedlings, mutant and wild-type seeds were separately germinated at high density in oil in 2×2 inches pots. The mutant seedlings were selected for herbicide resistance by spraying 0.2% commercial glufosinate ammonium when cotyledons were open. When seedlings were 10 days old, watering was withheld for 15 days before re-watering. To test more vigorously drought tolerance of the mutant at later developmental stages, one mutant plant was grown with one wild type in the same 5×5 centimeters pot under short-day conditions in the greenhouse. When plants were four weeks old, watering was withheld for 2 weeks. Water loss rate was measured in 10 plants each for the wild type and the hs1 mutant. Four-week-old plants were detached from their roots and weighed immediately. Then, the plant was placed in a plate on a laboratory bench and weighed at designated time intervals. The proportion loss of fresh weight was calculated on the basis of the initial weight of the plant.

The results in Table 3 further demonstrate that the drought tolerance and herbicide resistance co-segregated.

TABLE 3

Co-segregation analysis of drought tolerance with herbicide resistance.

| | Number of segregates | Number of herbicide resistant segregates | Number of drought tolerant segregates | $\chi^2$ (1:2:1) |
|---|---|---|---|---|
| Homozygote | 23 | 23 | 23 | 0.353 |
| Heterozygote | 52 | 52 | 52 | |
| Wildtype | 27 | 0 | 0 | |

Selfing and backcrossing were repeated, and the drought-tolerance phenotype and other phenotypes persisted generation after generation. Taken together, these results firmly establish a tight genetic linkage between the drought-tolerance phenotype and the T-DNA insertion. Moreover, the drought-tolerance phenotype is controlled by a single dominant locus, which suggests that the enhancers residing on the T-DNA might have activated a gene(s) at the integration site of the T-DNA.

2. Response to Drought Stress of Mutant T2 Segregation Population

A mutant T2 segregation population is randomly cultivated in soil (under the same condition). Four weeks later, the resistance to herbicide was assayed with paintbrush method on one leaf per plant to identify the genotypes. Yellow leaf indicates the wildtype. Meanwhile drought stress (without watering) was imposed for two weeks. The drought sensitive phenotype was associated with the wildtype, thus confirming drought tolerance phenotype co-segregated with the T-DNA with herbicide resistance bar gene.

3. Comparison of Drought Tolerance Between the Wild Type and the Mutant in the Same Pot To test more vigorously the drought tolerance, the heterozygous mutant and wild-type plants were grown in the same pot for better comparison. After two weeks without watering, the mutant plants showed only mild drought stress symptoms, while severe drought symptoms occurred in the wild-type plants. The assay unambiguously demonstrated the improved drought tolerance of the mutant. The homozygous mutant plants showed even stronger drought tolerance under these conditions (but were not included in this experiment, because their reduced size made it difficult to compare to the wild type.

Figure 2:
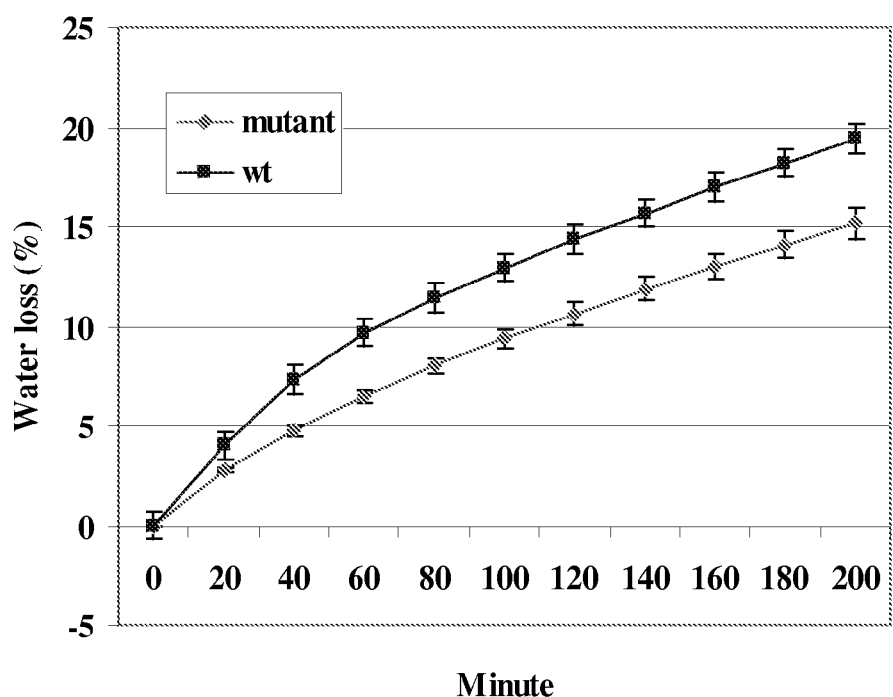
FIG. 2 is a graph showing comparison of the water loss rate of detached leaves in the air between the wild type and the mutant. Fresh weight was measured at the indicated times and water loss expressed as the percentage of the initial fresh weight (Values are mean+/−SE, n=20 plants).
Figure 3:
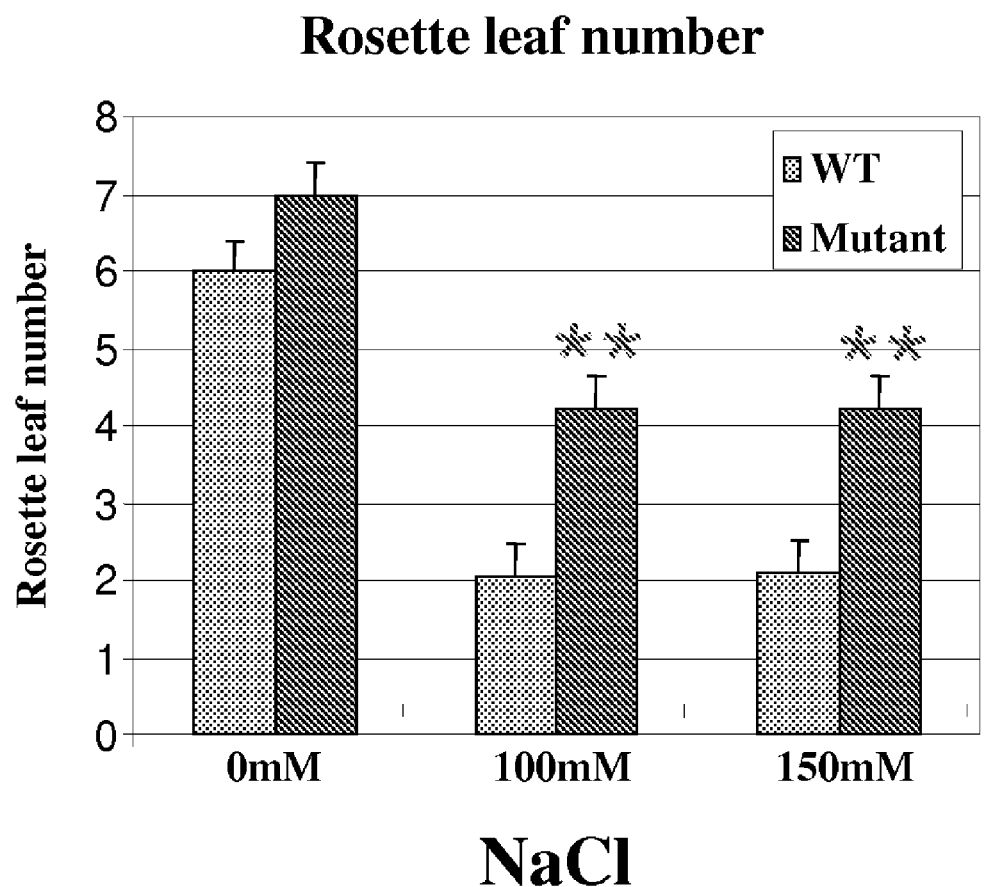
FIG. 3 is a graph showing comparison between the wild type and the mutant seedlings in response to salt stress. The asterisk indicates statistically significant differences *P<0.05, **P<0.01.

4. Comparison of Water Loss Rate of Detached Leaves Between the Mutant and the Wild Type Reduced transpirational water loss rate is a major factor contributing to drought tolerance. The mutant and the wild type are grown in the same tray, after four weeks rosette leaves were detached and their water loss rate determined in the air by weighing fresh weight every 20 minutes. Water loss rate is expressed as %=(initial weight−weight at a specific time point)×100/initial weight. FIG. 2 shows the water loss rate of the wild type leaf is faster than that of the mutant leaf. The slowed water loss from leaves is likely one of the major factors contributing to drought tolerance of the mutant. The other major factor is likely the enhanced root system of the mutant.

EXAMPLE 3

Response of the Mutant to Salt Stress in Contrast to the Wildtype

The mutant and the wild type are cultivated in the same tray under same growth conditions. Four weeks later salt stress was imposed by watering 0.2M NaCl solution. After 18 days salt stress, the salt stress phenotype was observed, where the wild type died and the mutant continued to grow. This demonstrates that the mutant has improved tolerance to salt stress, too.

The mutant and the wild type seeds were germinated on MS medium without salt. One week later, the seedlings were transferred to the medium containing 100 mM and 150 mM NaCl and let them continue to grow. The leaf number (as an indicator of continued growth under salt stress) was counted. The leaf number of the mutant is higher than that of the wild type under salt stress. ("wt" refers to wild type).

EXAMPLE 4

Response of the Mutant to Oxidation Stress in Contrast to the Wildtype

Drought stress leads to the accumulation of reactive oxygen species that need to be detoxified in order for plants to achieve drought tolerance (Chaves and Oliveira 2004; Wang et al. 2005 J Exp Bot 55(407): 2365-2384.). To test whether the enhanced drought tolerance in the mutant might involve alterations in oxidative stress responses, we compared the responses of the mutant and wild type seedlings to paraquat. SOD activity was determined. (Hodges and Forney 2000 J Exp Bot 51(344): 645-655). The reaction mixture includes 65.0 mM potassium phosphate (pH 7.5), 0.01 mM EDTA, 0.5 mM xanthine, 0.13 mM cyctochrome C, and 0.025 units xanthine oxidase. SOD activity was determined by monitoring the inhibition of the reduction rate of cyctochrome C between the reaction mixture and the control without protein extract (up to 200 ug protein) at 500 nm.

Figure 4:
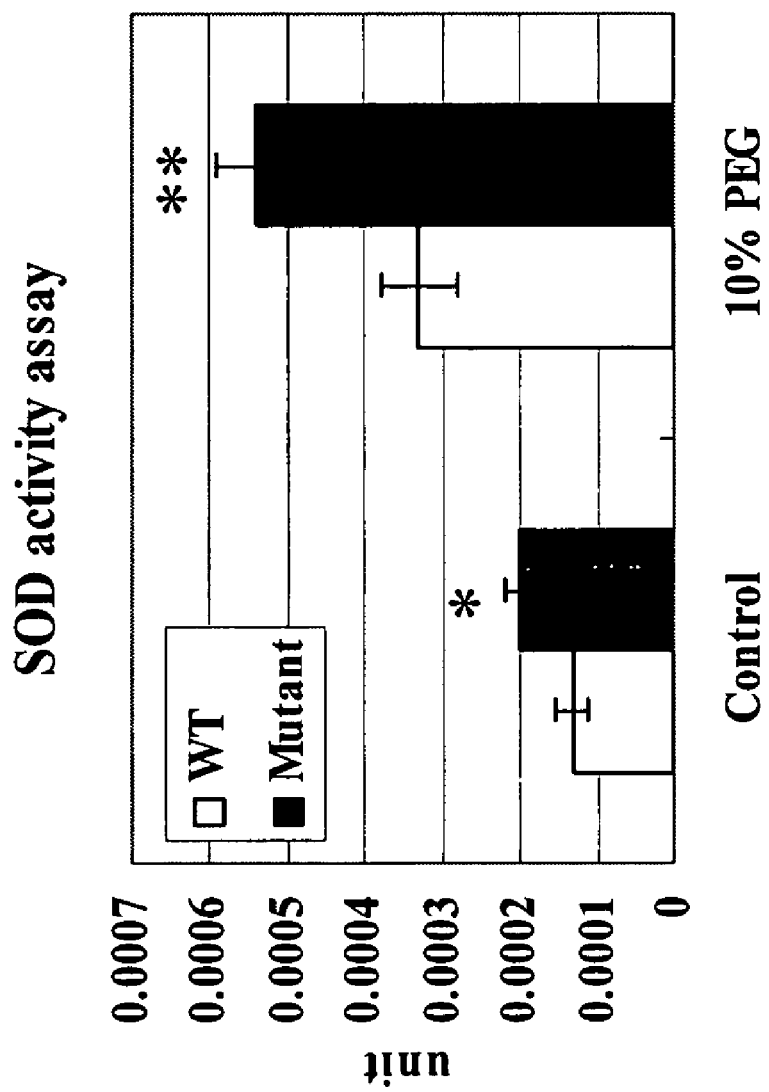
FIG. 4 is comparison of SOD activity between the hs1 mutant and the wild type (Values are mean+/−SE, n=3 experiments, the asterisk indicates statistically significant differences *P<0.05, **P<0.01).

The mutant and the wild type seeds were germinated on MS medium without paraquat. One week later, the seedlings-were transferred to the medium containing 0.2 mM and 2.0 mM paraquat and let them continue to grow for two weeks. Mutant seedlings were more tolerant paraquat that the wildtype that were bleached on the same medium. Paraquat at 0.2 µM caused complete bleaching of the wild type but not mutant plants, indicating that the mutant was substantially more tolerant to oxidative stress. SODs are important antioxidant enzymes detoxifying superoxide free radicals (Van Camp et al. 1990 Proc Natl Acad Sci U S A 87(24): 9903-9907; Arisi et al. 1998 Plant Physiol 117(2): 565-574; Kliebenstein et al. 1998 Plant Physiol 118(2): 637-650). That the hs1 mutant showed more tolerance to paraquat than the wild type indicates an enhanced capability to scavenge reactive oxygen species. Consistent with this notion, SOD activity assays showed a significantly higher activity in the mutant than the wild type. See FIG. 4. The elevated SOD activity was positively correlated with the SOD transcript levels as revealed by RT-PCR analysis. It is known that SODs are inducible by ABA (Guan and Scandalios 1998 Plant Physiol 117(1): 217-224; Jiang and Zhang 2002 J Exp Bot 53(379): 2401-2410).

EXAMPLE 5

ABA Accumulation is Altered in the Mutant in Response to Stress Treatments

ABA plays crucial roles in plant stress responses, especially during drought stress. To determine whether ABA metabolism is changed in the hs1 mutant, we first used ELISA to quantify the ABA content of the mutant and the wild type grown under the same conditions and treatments. Under normal conditions, the ABA content was not significantly different between the mutant and the wild type as showing in FIG. 5A.

ABA measurements were conducted as described (Yang et al. 2001 Plant Physiol 127(1): 315-323). Ten-day-old seedlings of the hs1 mutant and wild-type grown on ½×MS agar plates were transferred into ½×MS liquid medium supplemented with 150 mM NaCl or 10% PEG 6000 and incubated at 22° C. under continuous light for two days. One gram of the seedlings was used for ABA quantification by the ABA immunoassay kit as described (Yang 2001 Plant Growth Regulator 35: 233-237).

Upon exposure to 10% PEG 6000, a stress treatment commonly used to mimic drought tolerance in the laboratory, the ABA content was significantly higher in the mutant than in the wild type. These results implicate that input stress signals are required for the higher ABA accumulation in the mutant and the mutation may be involved in stress signaling. In addition, the nature ABA synthesis being activated by itself should also contribute to the observed higher level of ABA. The increased ABA content in the mutant under osmotic stress is consistent with its reduced water loss rate.

EXAMPLE 6

Proline Accumulation is Increased in the Mutant

Proline is considered an important osmoprotectant in drought stress response (Kishor et al. 1995 Plant Physiol 108(4): 1387-1394). Proline was found to serve as a potent antioxidant (Chen and Dickman 2005 Proc Natl Acad Sci U S A 102(9): 3459-3464). Ten-day-old seedlings of the hs1 mutant and wild-type grown on ½×MS agar medium containing 2% sucrose were transferred into ½×MS liquid medium supplemented with 10% PEG 6000 and incubated at 22° C. under continuous light for two days. Proline concentration was determined as described (Bates 1973 Plant Soil 35: 205-207).

Figure 5:
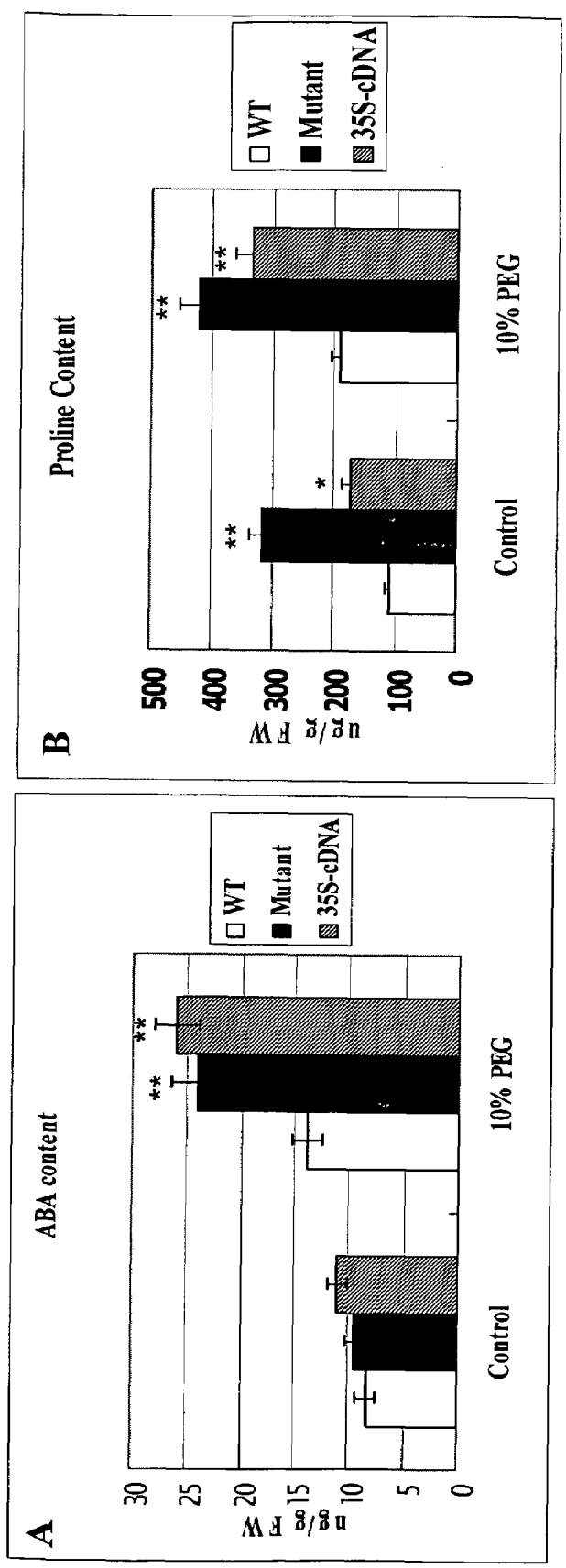
FIGS. 5A and B are two graphs, with 5A showing ABA content of tend day old seedlings determined by ELISA and 5B shows proline content spectrophotometrically measured. (Values are mean+/−SE, *P<0.05, **P<0.001)

Proline quantification results show a significant difference between the hs1 mutant and the wild type under stressed or unstressed conditions (see FIG. 5B). Under normal unstressed conditions, proline content was more than 300 μg per gram fresh weight in the mutant, which was 3-fold as much as that in the wild type. The PEG treatment increased the proline level to more than 400 μg/g fresh weight in the mutant, which was more twice as high as that in PEG-treated wild type. The elevated proline level in the mutant is likely another important beneficial factor for the mutant to cope with drought stress. Proline synthesis is activated by ABA and drought stress. The slightly increased ABA content does not seem to be sufficient for the significantly higher proline accumulation in the mutant under normal condition. This may be possible only if the proline synthesis pathway is more sensitive to ABA signaling. The other possibility might be the increased metabolic activities in the mutant where significantly elevated levels of several amino acids including glutamate, the precursor for proline synthesis, serine, glycine, threonine, and glutamine were observed by amino acid profiling.

EXAMPLE 7

The Cloning and Expression Analysis of the Tagged Gene

Step two of example two shows that the drought tolerance phenotype co-segregated with the bar gene, which strongly suggests that the enhanced stress tolerance phenotype is related to the T-DNA tagging and gives sufficient proof to clone the tagged gene.

1. The Cloning of the T-DNA Tagged Gene

First, a southern blotting experiment using bar gene as probe was performed as described (Xiang et al., 1997 DNA-binding properties, genomic organization and expression pattern of TGA6, a new member of the TGA family of bZIP transcription factors in *Arabidopsis thaliana*. Plant Mol Biol. 34:403-15.) and identified that the T-DNA in the genome was a single copy. Then, the plasmid rescue method was used to isolate the T-DNA insertion site as described (Weigel et al., 2000, Activation tagging in *Arabidopsis*. Plant Physiol. 122:1003-13). The tagged gene was identified by sequencing the T-DNA insertion junction. The nucleotide sequence of the tagged gene is shown in SEQ ID NO: 1 in the sequence table, and the amino acid residue sequence encoded by the gene is shown in SEQ ID NO: 2 in the sequence table. The gene is named AtHD/START1.

Figure 6:
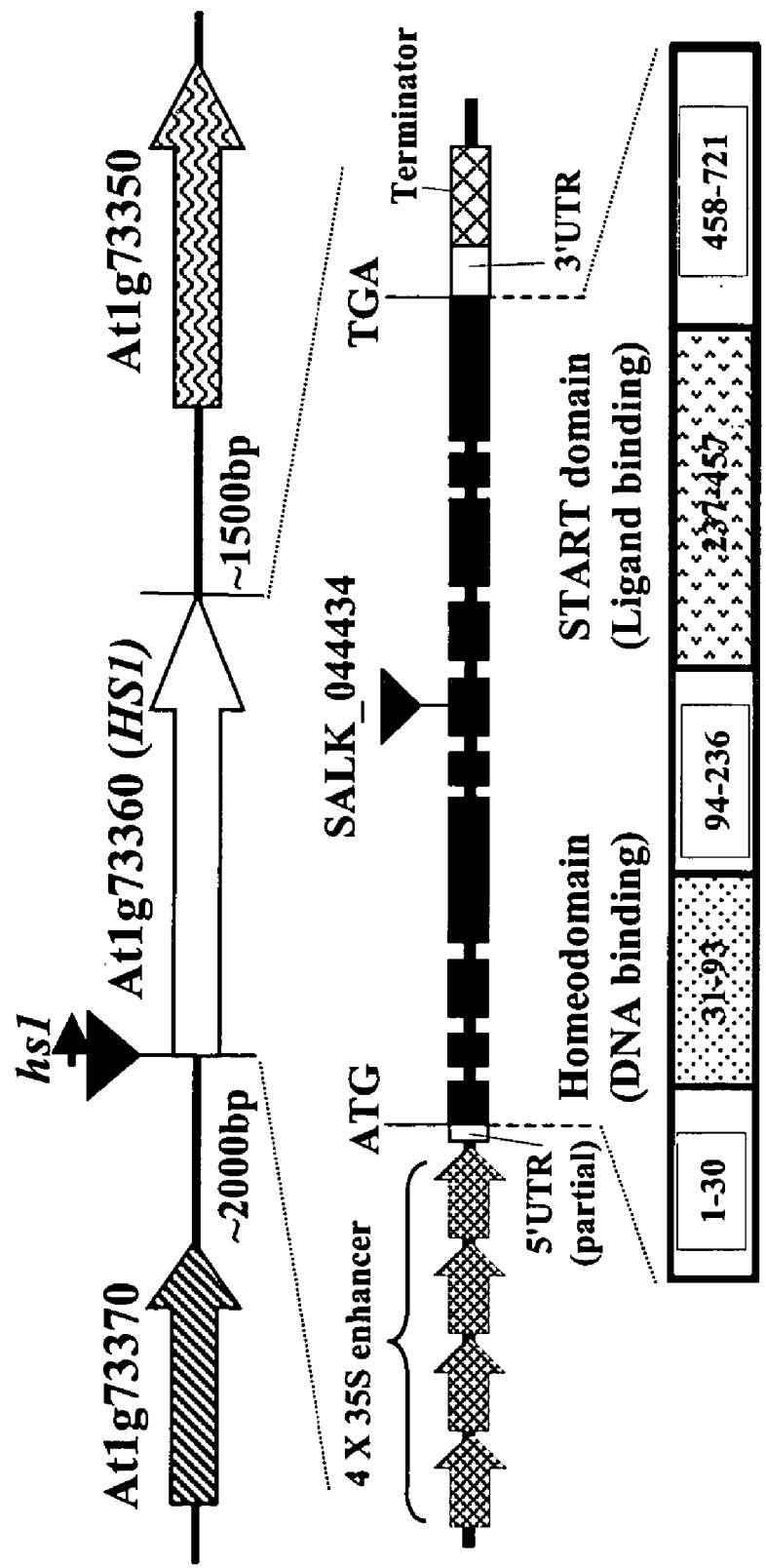
FIG. 6 shows the chromosomal location of the T-DNA insertion and locus At1g73360. Relative location (inverted solid triangle) and orientation (small arrow) of the T-DNA are shown in the upper panel. The T-DNA insertion in the SALK line is shown in the lower panel as an inverted triangle.

Subsequent sequencing with the T-DNA right border primer revealed that the T-DNA was inserted in the 5' UTR of At1g73360 on chromosome 1. The exact site of the integration of the T-DNA right border with four 35S enhancers was 50 pb upstream of the ATG initiation codon of At1g73360 (FIG. 6). The T-DNA insertion did not disrupt the rest of the gene and the coding region is identical to that of the wildtype.

The predicted At1g73360 locus consists of 10 exons and 9 introns. The ORF is predicted to encode a protein of 722 amino acids with an estimated molecular mass of 79 kDa. All these predictions were confirmed by sequencing the cloned cDNA. A BLAST search revealed that the gene encodes a homeodomain-START transcription factor with a homeodomain (HD) near the N-terminus and a START domain in the middle (FIG. 6). The At1g73360 gene is therefore named HS1. This type of protein with a combination of homeodomain plus START domain is only found in plant genomes.

The BLAST search result with the AtHD/START1 sequence shows that there are at least 17 members in this gene family in *Arabidopsis thaliana* genome. The homology of amino acid residue sequence between *Arabidopsis thaliana* AtHD/START1 (At1g73360) and its family members are At1g17920 (80%), At4g21750 (66%), At4g04890 (66%), At1g05230 (65%), At3g61150 (65%), At4g00730 (63%), At5g52170 (60%), At5g46880 (60%), At2g32370 (58%), At3g03260 (58%), At4g17710 (58%), At5g17320 (57%), At1g79840 (57%), At1g34650 (57%), At4g25530 (51%), and At5g07260 (46%), respectively. Two structural domains found are HD and START. HD is a DNA specific-binding domain and START is a hypothetical ligand binding domain. The HD domain in SEQ ID NO: 2 is at residues 31 to 93 (SEQ ID NO: 3) and the START domain I found at residues 237 to 458. (SEQ ID NO: 4)

2. The Expression Analysis of AtHD/START1

RT-PCR analysis indicated that HS1 expression was undetectable in vegetative tissues but the gene was expressed at low levels in the reproductive organs of the wild type. This is consistent with the *Arabidopsis* MPSS result for this gene (mpss.udel.edu/at/). The expression of HS1 gene was greatly altered in the mutant, in which high levels of HS1 transcript were detected in all organs analyzed. The altered expression pattern and elevated transcript levels of HS1 were apparently caused by the T-DNA insertion. Since the four tandem repeats of the 35S enhancers were inserted in the 5' UTR, the regulation by the HS1 promoter was likely abolished. Instead, the 35S enhancers caused strong expression of HS1 in a constitutive fashion. The HS1 transcript level is significantly higher in the homozygous mutant than in the heterozygote, suggesting that the strong phenotype of the homozygote is coffelated with the high level expression of HS1. The 35S enhancers may also act on other genes nearby or in some distance, which might also contribute to the mutant phenotype. RT-PCR analysis of the neighboring genes At1g73350 and At1g73370 revealed that their expression was not affected by the T-DNA insertion.

RT-PCR analysis indicated that HS1 expression was undetectable in vegetative tissues but the gene was expressed at low levels in the reproductive organs of the wild type. This is consistent with the *Arabidopsis* MPSS result for this gene (mpss.udel.edu/at/). The expression of HS1 gene was greatly altered in the mutant, in which high levels of HS1 transcript were detected in all organs analyzed. The altered expression pattern and elevated transcript levels of HS1 were apparently caused by the T-DNA insertion. Since the four tandem repeats of the 35S enhancers were inserted in the 5' UTR, the regulation by the HS1 promoter was likely abolished. Instead, the 35S enhancers caused strong expression of HS1 in a constitutive fashion. The HS1 transcript level is significantly higher in the homozygous mutant than in the heterozygote, suggesting that the strong phenotype of the homozygote is correlated with the high level expression of HS1. The 35S enhancers may also act on other genes nearby or in some distance, which might also contribute to the mutant phenotype. RT-PCR analysis of the neighboring genes At1g73350 and At1g73370 revealed that their expression was not affected by the T-DNA insertion.

The AtHD/START1 (marked gene) was not detectable in the wild type *Arabidopsis*, while highly expressed in the leaves of both homozygous (+/+) and heterozygous (+/−) mutant. The expression of the gene was totally correlated with stress tolerance phenotype, which not only confirmed that the mutation was indeed a functional activation mutation but also strongly suggested that the over expression of the gene was the direct cause of the enhanced stress tolerance phenotype.

EXAMPLE 8

Analysis of the Loss-of-HS1 Mutant, the Response of HS1 to Stress Treatments, and the Localization of HS1 Protein A T-DNA insertion mutant line SALK_044434 was obtained and its homozygous lines were screened by genomic PCR and confirmed by RT-PCR. A T-DNA insertion line SALK_044434 was obtained from ABRC and screened for homozygous progeny as described using HS1-specific primers and the T-DNA primer suggested (Alonso et al. 2003 Science 301(5633): 653-657). Despite the knockout of the HS1 gene, no apparent morphological difference was observed between the wildtype and the mutant throughout the development. Drought tolerance assay results indicate that the sensitivity to drought stress of the HS1 knockout mutant was not different from that of the wildtype. Considering the existence of closely related gene sequences in *Arabidopsis* genome, functional redundancy is one possibility for the knockout phenotype indifferent from the wildtype. Alternatively, HS1 may not be involved in stress tolerance in the wildtype. Another T-DNA insertion mutant for HS1 from Syngenta showed similar phenotypes.

RNA blot analysis was conducted to find if HS1 is responsive to drought and other abiotic stresses.(Xiang et al. 1997 Plant Mol Biol 34(3): 403-415) HS1 does not respond to PEG or ABA treatment, or to salt or oxidative stress. This is consistent with the compiled microarray data on TAIR website (www.arabidopsis.org). This result demonstrates that HS1 is not involved in drought stress response in the wildtype plants.

Homeodomain transcription factors are nuclear protein. To demonstrate that HS1 is localized in the nucleus, the HS1 cDNA was fused to the N-terminus of GFP. The fusion construct was delivered into onion epidermal cells. (Varagona et al. 1992 Plant Cell 4(10): 1213-1227) The nuclear localization of the HS1-GFP fusion protein was noted, demonstrating that HS1 accumulates in the nucleus.

EXAMPLE 9

Figure 7:
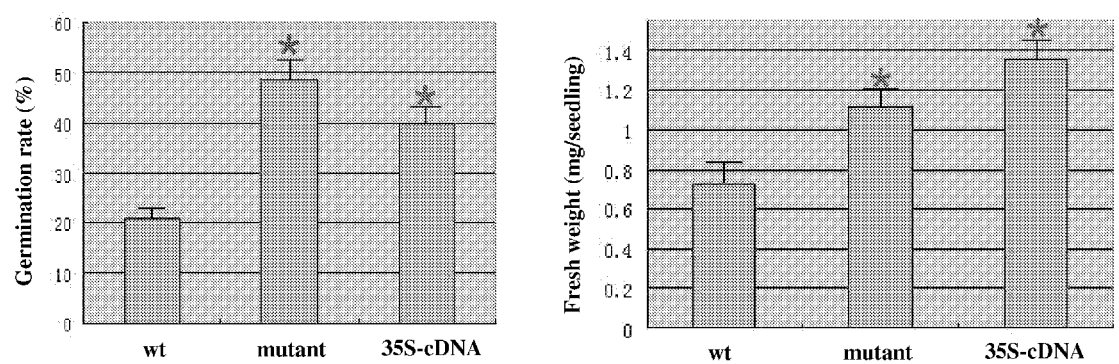
FIG. 7 is two graphs showing germination rate and fresh weight of the 35S-cDNA transformant, the mutant, and the wild type seeds under salt stress (150 mM NaCl). The asterisk indicates statistically significant differences *P<0.05.

Recapitulation of the Stress Tolerance Phenotype by Over Expression of AtHD/START1 cDNA in the Wild Type To confirm whether it is the activated expression of HS1 that causes the drought tolerance mutant phenotypes, recapitulation experiments were conducted. We cloned HS1 cDNA into an expression binary vector where the CaMV 35S promoter drives the expression of the HS1 cDNA and generated transgenic lines. In addition, the AtHD/START1 cDNA was also first cloned into vector pGEM-Teasy (T-A cloning). Then the AtHD/START1 cDNA fragment was cut out with restriction endonuclease SacI and SalI and ligated to the vector pCB302-3 opened with SpeI and SstI restriction site with the help of SacII/SpeI and SstI/SalI linkers (Xiang et al., 1999. A mini binary vector series for plant transformation. Plant Mol Biol. 40:711-7.). The resultant construct was transformed into *Arabidopsis* by use of *Agrobacterium* transformation using binary vectors, as described (Xiang et al., 2001. The biological functions of glutathione revisited in *Arabidopsis* transgenic plants with altered glutathione levels. Plant Physiol. 126:564-74). To observe the response of germination to salt stress (150 mM NaCl), the transgenic, the mutant, and the wild type seeds were germinated on the MS medium containing 150 mM NaCl for a week and the results are shown in FIG. 7. Like the mutant, both germination rate and fresh weight of the transformant overexpressing AtHD/START1 cDNA were significantly higher than those of the wild type.

Figure 8:
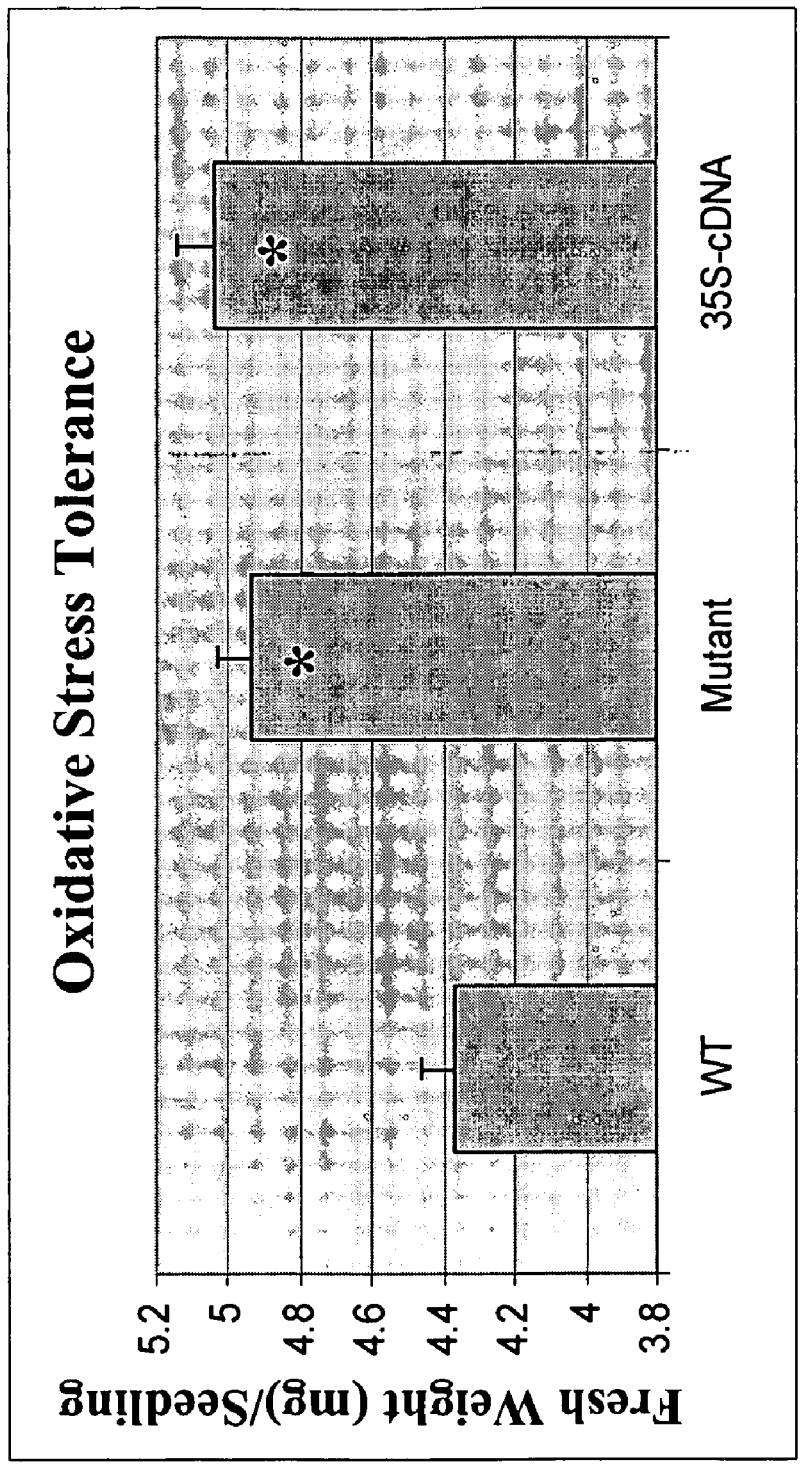
FIG. 8 is a graph showing comparison of response to oxidative stress (paraquat treatment) between the 35S-cDNA transformant, the mutant, and the wild type. The asterisk indicates statistically significant differences *P<0.05.

To assay the response to oxidative stress, one week old seedlings of transformant overexpressing AtHD/START1 cDNA 35S-cDNA transformant, the mutant and the wild type were grown on the MS culture containing 1 μM paraquat for one week to observe the response of seeding to oxidative stress, and the results are shown in FIG. 8. Both the mutant and the transformant overexpressing AtHD/START1 cDNA are significantly higher than the wild type in average plant fresh weight which indicates that the mutant and the transformant are more tolerant to oxidative stress than the wild type.

Figure 9:
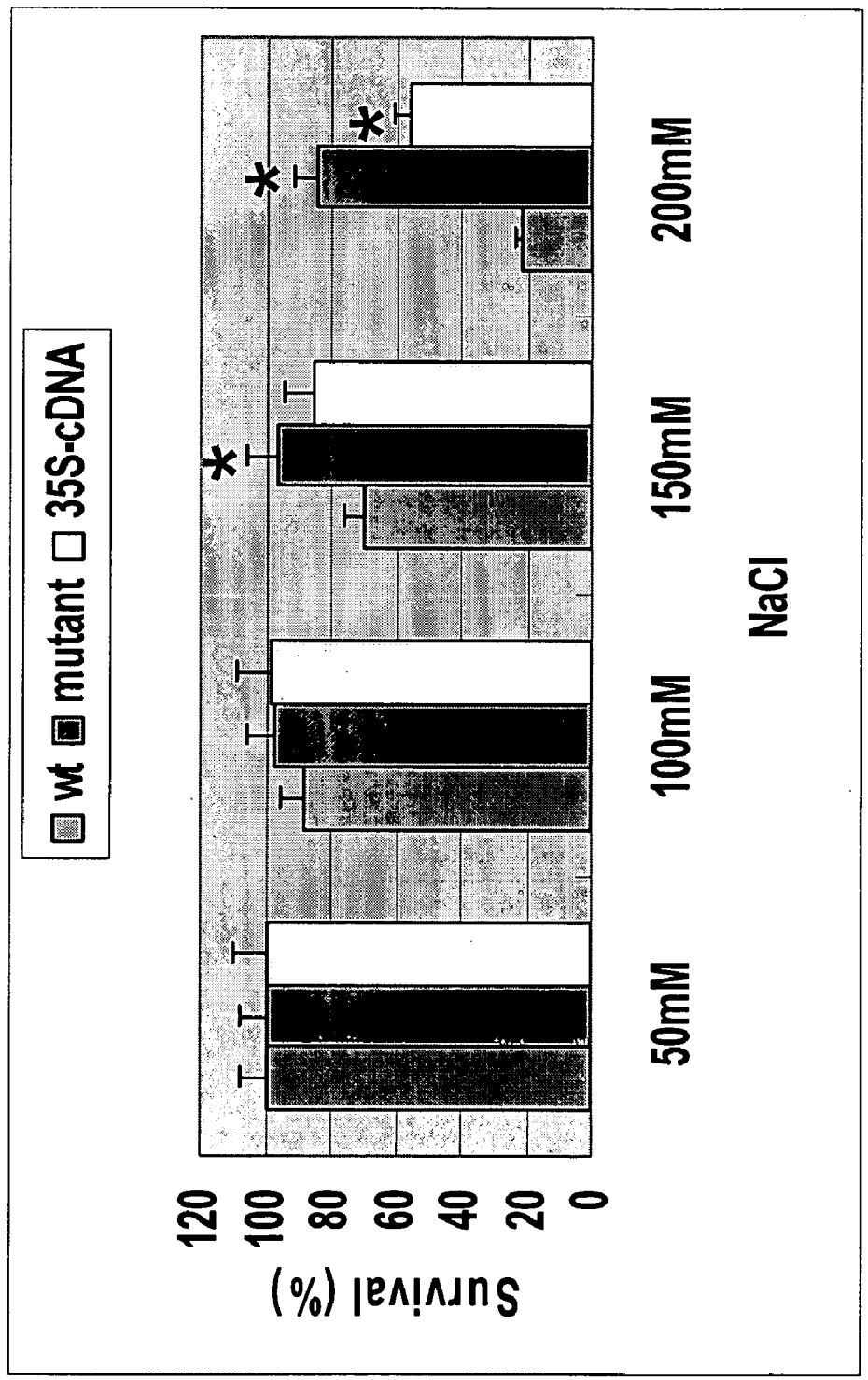
FIG. 9 is a graph showing comparison of survival ratio between the 35S-cDNA transformant, the mutant, and the wild type under different salt concentrations. The asterisk indicates statistically significant differences *P<0.05.

To observe the survival rate under different salt stress, the seeds of the transformant overexpressing AtHD/START1 cDNA-35S-cDNA transformant, the mutant, and the wild-type were grown on the MS medium containing different NaCl concentrations for 30 days. The results in FIG. 9 show that the survival rates of the transformant and the mutant are much higher than the wild type under 150 and 200 mM NaCl stress.

Figure 10:
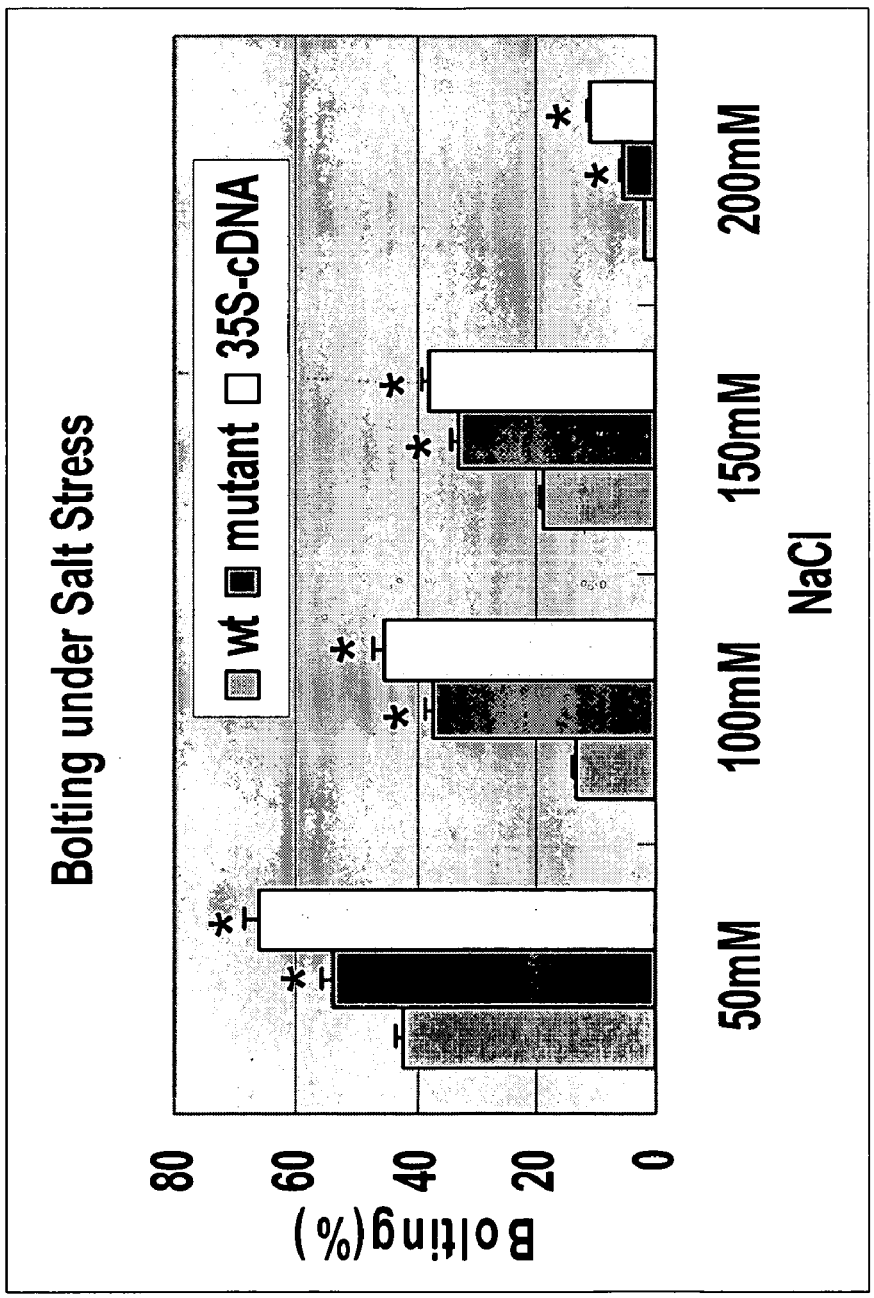
FIG. 10 is a graph showing comparison of bolting frequency between the wild type, the mutant, and the 35S-cDNA transformant under different salt concentrations.

The seeds of transformant overexpressing AtHD/START1 cDNA-35S-cDNA transformant, the mutant, and the wild type were also germinated and grown in soil and subjected to salt stress of different NaCl concentrations. Bolting frequency was observed for each treatment and the bolting frequency-of the transformant and the mutant is much higher than that of the wild type under all four salt concentrations used in the experiment. See FIG. 10.

Figure 11:
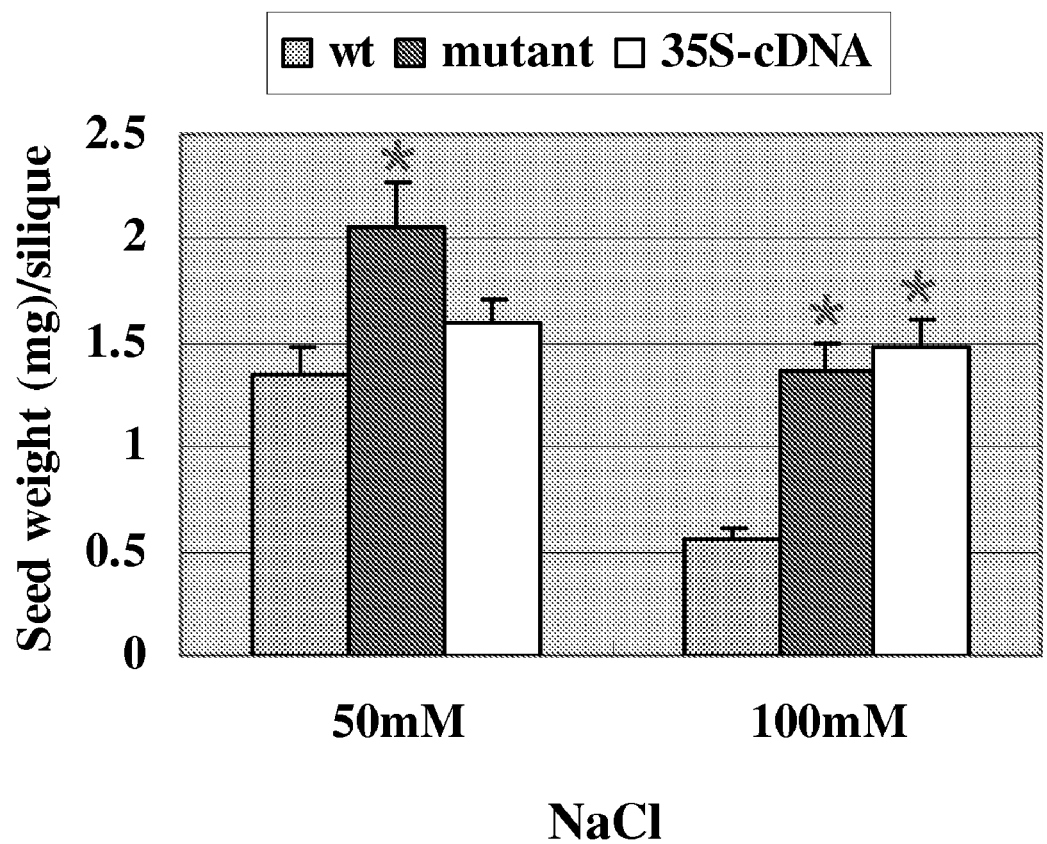
FIG. 11 is a graph showing comparison of silique weight between the wild type, the mutant, and the 35S-cDNA transformant under different salt concentrations.
Figure 12:
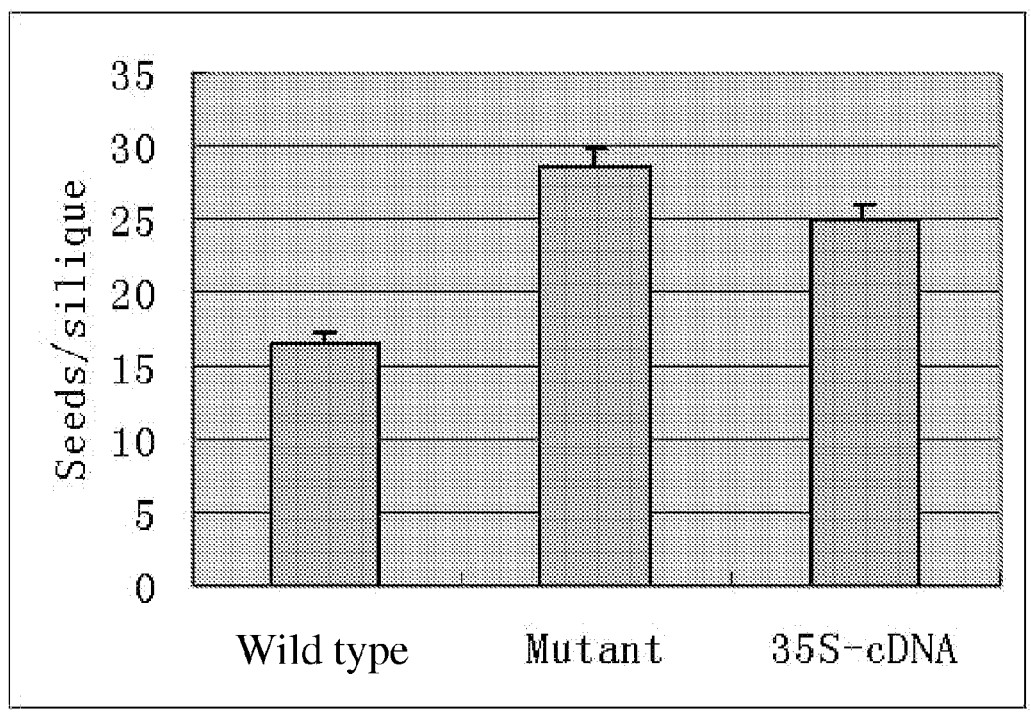
FIG. 12 is a graph showing comparison of silique seed yield between the wild type, the mutant, and the 35S-cDNA transformant under 100 mM NaCl stress.

To observe the weight of silique under different salt stress, the number of seeds in silique under 100 mM NaCl, the phenotype of silique, and plants, the seeds of transformant overexpres sing AtHD/START1 cDNA-355-cDNA transformant, the mutant and the wild type *Arabidopsis* were grown in soil and stressed with different NaCl concentrations till maturation. The results shown in FIGS. 11 and 12 indicated that the weight of silique of the transformant and the mutant (FIG. 11), and the number of seeds in silique shown in FIG. 12 are much higher than wild type under 100 mM NaCl. The silique and plants of the transformant and the mutant are much healthier than the wild type under 100 mM NaCl stress.

To test drought tolerance in soil, the 35S-cDNA over expression transformant and the wild type were grown in the same pot. Observation of the 3-week old 35S-cDNA over expression transformant and the wild type plants after drought stress for 2 weeks showed that the 35S-cDNA transformants are more drought tolerant than the wild type.

The transgenic plants displayed a gradient of phenotypes ranging from the wildtype to hs1 mutant. While this is typical of 35S-driven over expression of transgenes, it also suggests that the degree of mutant phenotypes (delayed flowering and rosette leaf number) is correlated with the expression levels of HS1. The HS1 over expressors showed significantly improved drought tolerance compared with the wild type grown in the same pot. Compared to wild type plants, the transgenic plants also showed reduced water loss rate from leaves. These results demonstrate that overexpressing the HS1 cDNA in the wild type can recapitulate the drought tolerance phenotype of the mutant. In addition, we have demonstrated that HS1 over expression-mediated drought tolerance appears to be well conserved in both dicots and monocots of HS1 since transgenic tobacco, turf grass, and rice expressing HS1 all showed enhanced drought tolerance.

The ABA and proline contents of the transgenic plants were all similar to those of the hs1 mutant and were significantly higher than those of the wild type (FIGS. 5A and B). Taken together, the recapitulation results confirm that the activated expression of the HS1 gene is the cause of the drought stress tolerance phenotypes in the mutant.

The experiments described above show that the improved stress tolerance phenotype can be recapitulated by expressing AtHD/START1 cDNA, implicating the great potential of this stress tolerance gene for crop improvement.

EXAMPLE 10

The Transcript Levels of Several Key Drought-responsive Genes are Elevated in the Mutant To begin to understand the HS1 regulon that underlies the drought tolerance function of HS1, we analyzed the transcript levels of several stress-responsive marker genes and key regulators, in response to drought stress treatment.

Seedlings were grown on ½×MS agar media pulsing 20 g/L sucrose under continuous light, and 10-days-old seedlings were treated with 30% PEG 6000 for 3 hours. Total RNA was prepared using TRIZOL reagent (Invitrogen) and 1 µg of RNA from each sample was used for reverse transcription. As an internal control, the tubulin transcript was used to quantify the relative transcript number of each target gene in each tissue type; values were calculated and statistically analyzed as described (Livak and Schmittgen 2001 Methods 25(4): 402-408).

The real-time RT-PCR results in Table 4 show that under normal conditions, the transcript level of the stress marker genes RD29A (Liu et al. 2000 Proc Natl Acad Sci USA 97(7): 3730-3734), P5CS (Kishor et al. 1995 Plant Physiol 108(4): 1387-1394), encoding the rate-limiting enzyme for proline synthesis, and NCED3, encoding the key enzyme in the ABA synthesis pathway (Chernys and Zeevaart 2000 Plant Physiol 124(1): 343-353), the stress- and ABA-responsive transcription factors, ABI3 (Giraudat et al. 1992 Plant Cell 4(10): 1251-1261), ABF4 (Kang et al. 2002 Plant Cell 14(2): 343-357), and DREB2 (Liu et al. 1998 Plant Cell 10(8): 1391-1406), was slightly higher in the mutant and transgenic lines than in the wild type. In response to PEG treatment, both the mutant and the transgenic lines had significantly higher level of transcript for all six genes examined than the wildtype.

TABLE 4

Relative expression level stress-responsive genes in response to stress treatment.

| | Control | | | 30% PEG6000 | | |
|---|---|---|---|---|---|---|
| | Wild Type | hs1 Mutant | 35S-cDNA | Wild Type | hs1 Mutant | 35S-cDNA |
| RD29A | 1.00 ± 0.10 | 1.88 ± 0.12 | 1.53 ± 0.12 | 93.70 ± 8.12 | 182.28 ± 15.80 | 172.45 ± 12.40 |
| P5CS | 1.00 ± 0.08 | 1.40 ± 0.14 | 1.29 ± 0.15 | 37.50 ± 2.17 | 150.12 ± 14.20 | 153.28 ± 14.50 |
| NCED3 | 1.00 ± 0.07 | 7.52 ± 0.59 | 6.77 ± 0.64 | 40.79 ± 2.92 | 178.53 ± 14.14 | 158.68 ± 16.20 |
| ABI3 | 1.00 ± 0.13 | 7.62 ± 0.78 | 8.82 ± 0.63 | 30.91 ± 1.99 | 256.00 ± 18.40 | 183.55 ± 13.20 |
| ABF4 | 1.00 ± 0.12 | 2.89 ± 0.29 | 2.97 ± 0.26 | 44.32 ± 3.85 | 235.57 ± 18.70 | 230.72 ± 14.90 |
| DREB2 | 1.00 ± 0.08 | 11.16 ± 0.97 | 10.56 ± 1.32 | 150.10 ± 11.90 | 494.56 ± 31.80 | 685.02 ± 49.20 |

These results show that these key regulators involved in drought stress response are more responsive to environmental cues in the hs1 mutant and the transgenic lines overexpressing the HS1 cDNA, which is consistent with the results of ABA accumulation. Again, the results also show that the ectopically expressed HS1 requires input stress signals to trigger a significant drought response since under normal conditions, it is not sufficient to elicit the full response, implicating that HS1 is involved in stress signaling and likely potentiates the stress responsiveness in the mutant and amplifies stress signaling upon stress stimulation. This response behavior is beneficial to plants and suitable for crop improvement, and different from other transcription factors such as DREB factors whose constitutive expression usually cause growth retardation (Kasuga et al. 1999 Nat Biotechnol 17(3): 287-291).

EXAMPLE 11

Figure 13:
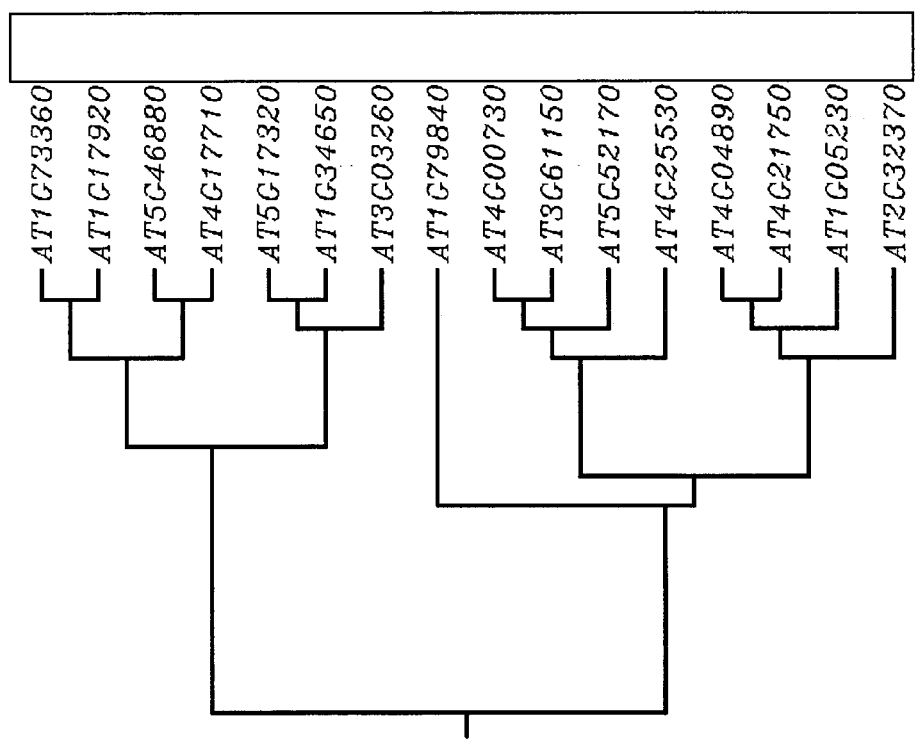
FIG. 13 is shows the phylogenetic tree with the full-length amino acid sequence.
Figure 14:
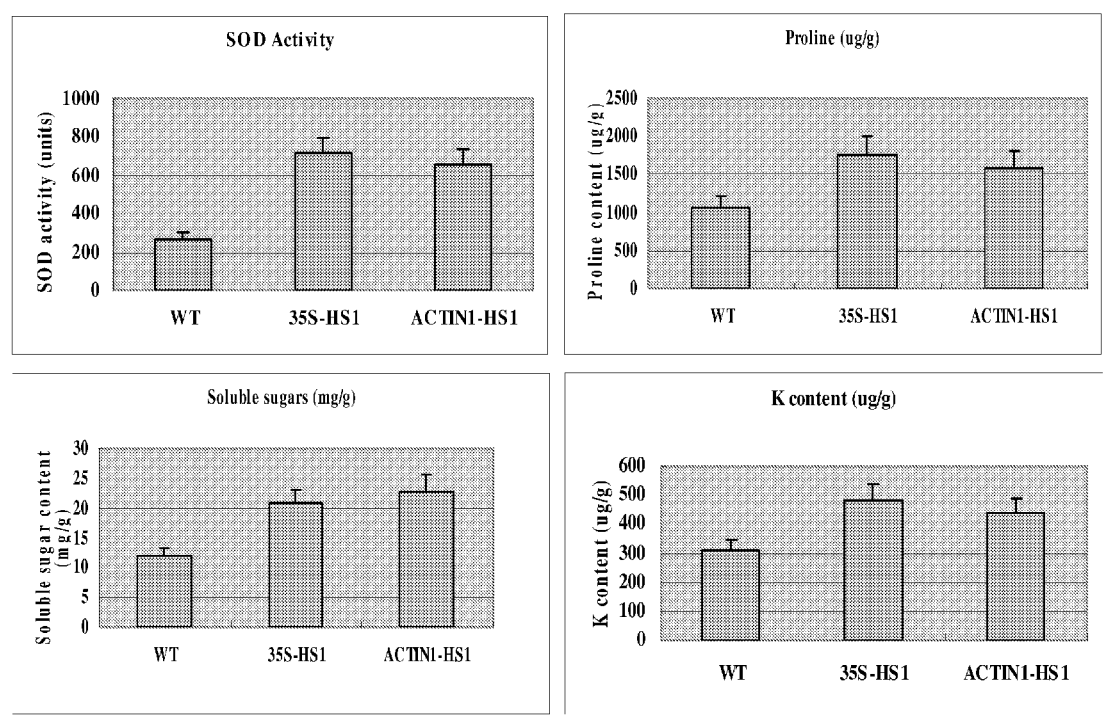
FIG. 14 is graphs showing increased proline, SOD and soluble sugar content compared between wild type and transgenic tobacco expressing HS1.

Homeodomain-START Gene Family in *Arabidopsis* Genome and Functional Survey for Stress Tolerance A fairly large homeodomain-START gene family exists in the *Arabidopsis* genome. Sixteen genes are found to have significant sequence homologies with HS1, ranging from 46% to 80%, at the amino acid level (Table 5) and the phylogenetic relation is shown in FIG. 13.

EXAMPLE 12

Transgenic Tobacco Expressing HS1

Figure 16:
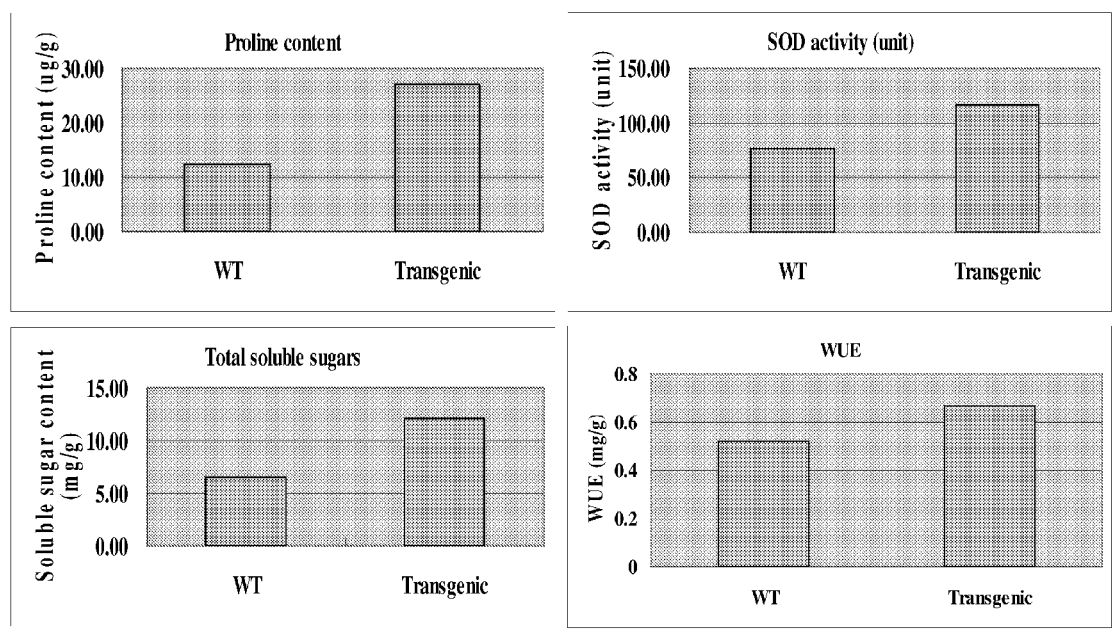
FIG. 16 is graphs comparing proline, SOD activity, total soluble sugars and water use efficiency compared between wild type and transgenic rice expressing HS1.

Using the *Agrobacterium* protocol and binary vectors described supra, tobacco was transformed with the HS1, driven by the 35S promoter. Tobacco was additionally transformed with the actin 1 promoter driving HS1 expression. Using the assays as outlined above, proline content, SOD activity, the amount of soluble sugars and potassium content was measured in wild type and transgenic tobacco. The results are shown in FIG. 16. Comparison of leaf cells and stomata between wild type and transgenic tobacco is set forth below.

TABLE 5

Comparison of wild type and transgenic tobacco leaf cells and stomata

| | Palisade cell length (μm) | Palisade cell width (μm) | Epidermal cell density (number/mm) | Stomatal length (μm) | Stomatal width (μm) | Stomatal density (number/mm) | Stomatal index (%) |
|---|---|---|---|---|---|---|---|
| WT | 67.77 | 27.60 | 265.83 | 33.26 | 25.98 | 103.63 | 28 |
| Transgenic | 135.83 | 50.36 | 173.45 | 43.00 | 31.63 | 46.05 | 21 |

TABLE 5

Functional survey of HD-START gene family for stress tolerance

| Family member | ID | Similarity to HS1 (aa) | cDNA or genomic DNA | Stress tolerance |
|---|---|---|---|---|
| HS1 | AT1G73360.1 | 100 | cDNA | Yes |
| HS2 | AT1G17920.1 | 80 | cDNA | Yes |
| PDF2 | AT4G04890.1 | 66 | cDNA | No |
| ATML1 | AT4G21750.1 | 66 | cDNA | No |
| HS3 | AT1G05230.1 | 65 | cDNA | No |
| ANL2 | AT3G61150.1 | 65 | cDNA | No |
| ANL2-like | AT5G52170.1 | 63 | cDNA | No |
| AHDP | AT4G00730.1 | 63 | cDNA | No |
| HS4 | AT5G46880.1 | 60 | Genomic | No |
| HS5 | AT2G32370.1 | 58 | Genomic | No |
| HS6 | AT3G03260.1 | 58 | Genomic | No |
| HS7 | AT4G17710.1 | 58 | Genomic | No |
| HS8 | AT5G17320.1 | 57 | Genomic | No |
| GL2 (AtHB10) | AT1G79840.1 | 57 | cDNA | No |
| HS9 | AT1G34650.1 | 57 | Genomic | No |
| FWA | AT4G25530.1 | 51 | Genomic | No |
| HS10 | AT5G07260.1 | 46 | cDNA | No |

This class of homeodomain transcription factors is unique to plants and absent from other kingdoms (Schrick et al. 2004 Genome Biol 5(6): R41). To assess whether other family members in the gene family confer stress tolerance when ectopically over expressed, we cloned the cDNAs or genomic DNA for all family members and created their plant expression constructs. The corresponding transgenic lines were generated for drought stress tolerance evaluation. At least 50 independent transgenic lines were generated and tested for each construct (Table 5). Only HS2, with the highest amino acid sequence similarity to HS1, conferred improved tolerance when over expressed in the wild type. These results suggest that the highly similar HS1 and HS2 genes can both confer stress tolerance when over expressed.

The plants expressing HS1 demonstrated improved SOD activity, proline and potassium content and soluble sugars. Further, the transgenic plants had more leaves, later flowering, reduce stomatal density (about 50%) and stomatal index, reduced cell density, and increased leaf thickness compared to non-transgenic plants, all allowing for improved tolerance in stress conditions. Drought tolerance was also measured by withholding water during the entire period, with the HS1 expressing plants showing improved tolerance through 36 days. Recovery upon resumption of water was also markedly improved as observed at two and five days.

EXAMPLE 13

Transgenic Rice Expressing HS1

Figure 15:
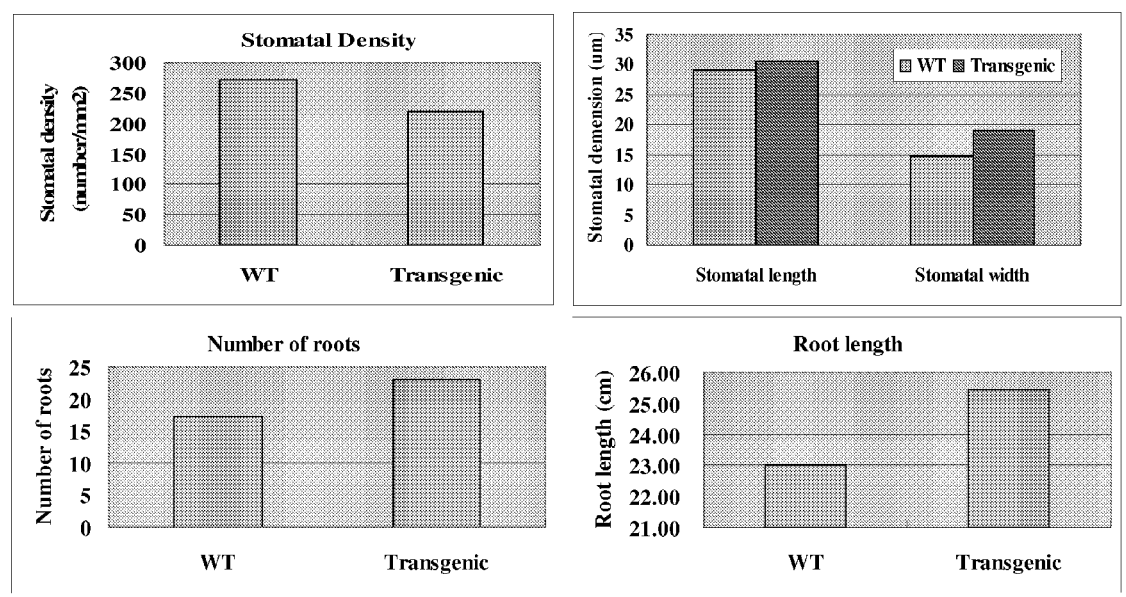
FIG. 15 is graphs comparing stomatal density and dimension, number of roots per plant and length of the longest root between the wild type and transgenic rice.

Again using the *Agrobacterium* protocol and binary vectors described supra, rice was transformed with HS1, driven by the actin 1 promoter with the nos terminator. The plants developed normally. When compared to wild type plants, under drought stress as outlined above, homozygous transgenic $T_2$ plants showed improved tolerance as observed at nine days and 14 days, and marked improvement in recovery with resumption of watering. Measurement of stomatal density, length and width, and the number or roots and root length of average of five independent lines is shown in the graphs of FIG. 15. FIG. 16 shows measurement of proline content, SOD activity, total soluble sugars and water use efficiency. The plants expressing HS1 therefore also demonstrate properties that improve resistance to stress.

INDUSTRIAL APPLICATION

The invention can not only be used to improve the tolerance of crops but also is very important to basic studies of plant stress biology.

What is claimed is:

1. A method of producing a transgenic plant having increased drought, salt or oxidative stress tolerance, the method comprising:
   (a) introducing into the plant an isolated nucleotide sequence comprising a sequence selected from the group consisting of: (i) the nucleotide sequence of SEQ ID NO: 1; (ii) a nucleotide sequence encoding a protein having the amino acid sequence of SEQ ID NO: 2, wherein expression of the nucleotide sequence increases drought, salt or oxidative stress tolerance in the plant compared to a non-transformed plant of the same species; and
   (b) screening for the plant having increased tolerance to drought, salt or oxidative stress tolerance compared to a non-transformed plant of the same species.

2. The method of claim 1 wherein the sequence is introduced into the plant by crossing a plant comprising the nucleotide sequence with a second plant lacking said nucleotide sequence, and screening for progeny plants that expresses the nucleotide sequence.

3. The method of claim 1 wherein the plant has increased drought tolerance compared to a non-transformed plant of the same species.

4. The method of claim 1 wherein the plant has increased salt tolerance compared to a non-transformed plant of the same species.

5. The method of claim 1 wherein the plant has increased oxidative stress tolerance compared to a non-transformed plant of the same species.

6. The method of claim 1, further comprising ascertaining plant properties selected from the group consisting of transpiration rate, stomatal density, stomatal index, stomatal length, stomatal width, cell density, leaf thickness, root architecture, root number, root length, germination rate, seedling fresh weight, silique seed number, silique weight, bolting frequency, and survival after drought, salt or oxidative stress.

7. The method of claim 1 further comprising measuring production in the transgenic plant of a composition selected from the group consisting of ABA and proline, and comparing production of said composition to a non-transformed plant of the same species, wherein the transgenic plant has increased ABA and proline content compared to the non-transformed plant of the same species.

8. The method of claim 1, further comprising measuring SOD activity in the transgenic plant and comparing the activity to SOD activity of a non-transformed plant of the same species, and wherein the transQenic plant has increased SOD activity compared to the non-transformed plant of the same species.

* * * * *